US012323400B2

(12) United States Patent
Kotlarz et al.

(10) Patent No.: US 12,323,400 B2
(45) Date of Patent: Jun. 3, 2025

(54) SYSTEM AND METHOD FOR ESTABLISHING SECURE COMMUNICATION AND AUTHENTICATION BY EMBEDDING PULSE CODES INTO CONTENT IN REAL-TIME

(71) Applicants: Michael Kotlarz, Short Hills, NJ (US); Keith Barksdale, Hoboken, NJ (US)

(72) Inventors: Michael Kotlarz, Short Hills, NJ (US); Keith Barksdale, Hoboken, NJ (US)

( * ) Notice: Subject to any disclaimer, the term of this patent is extended or adjusted under 35 U.S.C. 154(b) by 208 days.

(21) Appl. No.: 18/094,457

(22) Filed: Jan. 9, 2023

(65) Prior Publication Data

US 2023/0362138 A1 Nov. 9, 2023

Related U.S. Application Data

(60) Provisional application No. 63/339,153, filed on May 6, 2022.

(51) Int. Cl.
*H04L 9/40* (2022.01)
*G16H 10/60* (2018.01)

(52) U.S. Cl.
CPC ......... *H04L 63/0428* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 12,015,448 B1 * | 6/2024 | Chang | H04J 14/0227 |
| 2002/0191765 A1 * | 12/2002 | Labaton | G06Q 20/4097 |
| | | | 379/201.01 |
| 2009/0313465 A1 * | 12/2009 | Verma | H04Q 11/0066 |
| | | | 713/153 |
| 2011/0235427 A1 * | 9/2011 | Chen | G11C 16/10 |
| | | | 365/185.21 |
| 2018/0358113 A1 * | 12/2018 | Cronin | G06F 21/32 |
| 2020/0220722 A1 * | 7/2020 | Costello | H04L 63/0428 |
| 2021/0306160 A1 * | 9/2021 | Andoni | H04L 9/3268 |

* cited by examiner

*Primary Examiner* — Raqiul A Choudhury

(57) ABSTRACT

A system for establishing a secure communication or authentication in real-time, the system consists of a first computing device and a second computing device, each with a content encoding and decoding module. Each content encoding and decoding module includes a content selection module that allows a user to choose content and send it to a pulse injector, which embeds pulse codes using contextual, user-specific from devices or a cloud/external database. The pulse oracle authenticates and adjusts pulse codes continuously for security. The pulse reader receives content, and sends decoded pulse information to second computing device, establishing secure communication in real time over network.

20 Claims, 18 Drawing Sheets

SYSTEM AND METHOD FOR ESTABLISHING SECURE COMMUNICATION AND AUTHENTICATION BY EMBEDDING PULSE CODES INTO CONTENT IN REAL-TIME

CROSS-REFERENCE TO RELATED APPLICATIONS

This patent application claims priority benefit of U.S. Provisional Patent Application No. 63/339,153, entitled "COMPUTER-IMPLEMENTED SYSTEM AND METHOD FOR EMBEDDING PULSE CODES INTO CONTENT IN REAL-TIME", filed on 6 May 2022. The entire contents of the patent application is hereby incorporated by reference herein in its entirety.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

TECHNICAL FIELD

The disclosed subject matter relates generally to computer-implemented systems and methods for providing secure authentication in user communication. More particularly, the present disclosure relates to a computer-implemented system and method for embedding pulse codes into content to provide secure real-time communication, real-time certification, and real-time authentication.

BACKGROUND

Digital watermarks exist at a convergence point where creators and publishers of digitized multimedia content demand localized, secured identification and authentication of that multimedia content. Digital watermarking is old, static and does not adequately support the needs of dynamic digital content. In recent years, digital content has been distributed in growing quantities over the Internet. The digital content is constituted illustratively by text information, pictures, moving pictures, video games, and other publications converted into electronic data. As such, content is reproduced by personal computers for use, and the content is delivered to users over networks. In today's digitized society, this mode of content delivery poses a significant challenge: to authenticate authorized users to provide access and to continually monitor the use of content via real-time authentication and to bar and protect against unauthorized users.

Further, the massive growth in digital content and communications usage is a complex problem to secure, from unauthorized duplication, plagiarism to hacker theft of corporate and state secrets. The most modern authentication of digital content relies on passwords and encrypted keys. For example, Bitcoin uses a 256-bit encrypted key. The 256-bit encrypted key is static and can brute-force hack in a minimum duration of time once there is an actual quantum computer, and the bitcoin wallets risk becoming systematically emptied. Hence, there is a need to develop a real-time system for injecting dynamic objects/pulse codes/data/images into the content to ensure security, certifying authenticity, and improve automation.

In the light of the aforementioned discussion, there exists a need for a certain system with novel methodologies that would overcome the above-mentioned challenges.

SUMMARY

The following invention presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

An objective of the present disclosure is directed towards a system that enables seamless real-time secure communication, certification, and authentication across a wide variety of applications by embedding a robust dynamic and undetectable secure praxis within the content itself.

Another objective of the present disclosure is directed towards the system that provides a dynamic multidimensional and programmatic secure authentication of the content from static documents and photos to real-time video conferencing.

Another objective of the present disclosure is directed towards the system that embeds pulse codes within the content itself to provide secure self-authenticating platform-agnostic elements capable of interacting with applications and use cases.

Another objective of the present disclosure is directed towards the system that embeds micro pulse layers in the content that a hacker must locate, decode the Pulse, and provide precise context specific answers to multiple dynamic MicroPulse layers.

Another objective of the present disclosure is directed towards the system that does not allow the hacker to use brute force repetition to guess a password, a location, an acceptable IP address and/or a session-based 256-bit key.

Another objective of the present disclosure is directed towards the system dynamically updating the 256-bit encrypted key in every instance when there is a failed attempt.

Another objective of the present disclosure is directed towards the system that embeds and changes the pulse dynamically in real-time.

Another objective of the present disclosure is directed towards the system that customizes each Pulse as per creator, per user, or along with any number of configurable axes.

According to an exemplary aspect of the present disclosure, a system for establishing a secure communication in real-time, the system includes a first computing device, a second computing device, and a cloud server.

According to another exemplary aspect of the present disclosure, at least one computing device includes a content encoding and decoding module, and the content encoding and decoding module further includes a content selection module, a pulse injector, and a pulse reader.

According to another exemplary aspect of the present disclosure, the cloud server includes a pulse oracle, a pulse data manager, and an internal database.

According to another exemplary aspect of the present disclosure, the content selection module enables a first user to select content on the first computing device and send the content selected by the first user to the pulse injector, the pulse injector embeds pulse codes into the content selected by the first user, the pulse injector construct pulse codes by gathering a multidimensional data, from at least one internal database established in the cloud server and any number of external databases.

According to another exemplary aspect of the present disclosure, the pulse oracle and the pulse reader are synchronized to receive the pulse codes and authenticate the pulse codes embedded in the content selected by the first user, the pulse oracle changes each individual pulse code and underlying micro pulses programmatically and continuously in the content.

According to another exemplary aspect of the present disclosure, the pulse reader receives the authenticated pulsed content selected by the first user from the pulse oracle and decodes pulse information from the authenticated pulsed digital content, the pulse reader sends the decoded pulse information to the second computing device of a second user and establishes a secure communication in real time over the network.

BRIEF DESCRIPTION OF THE DRAWINGS

In the following, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

Figure 1A:
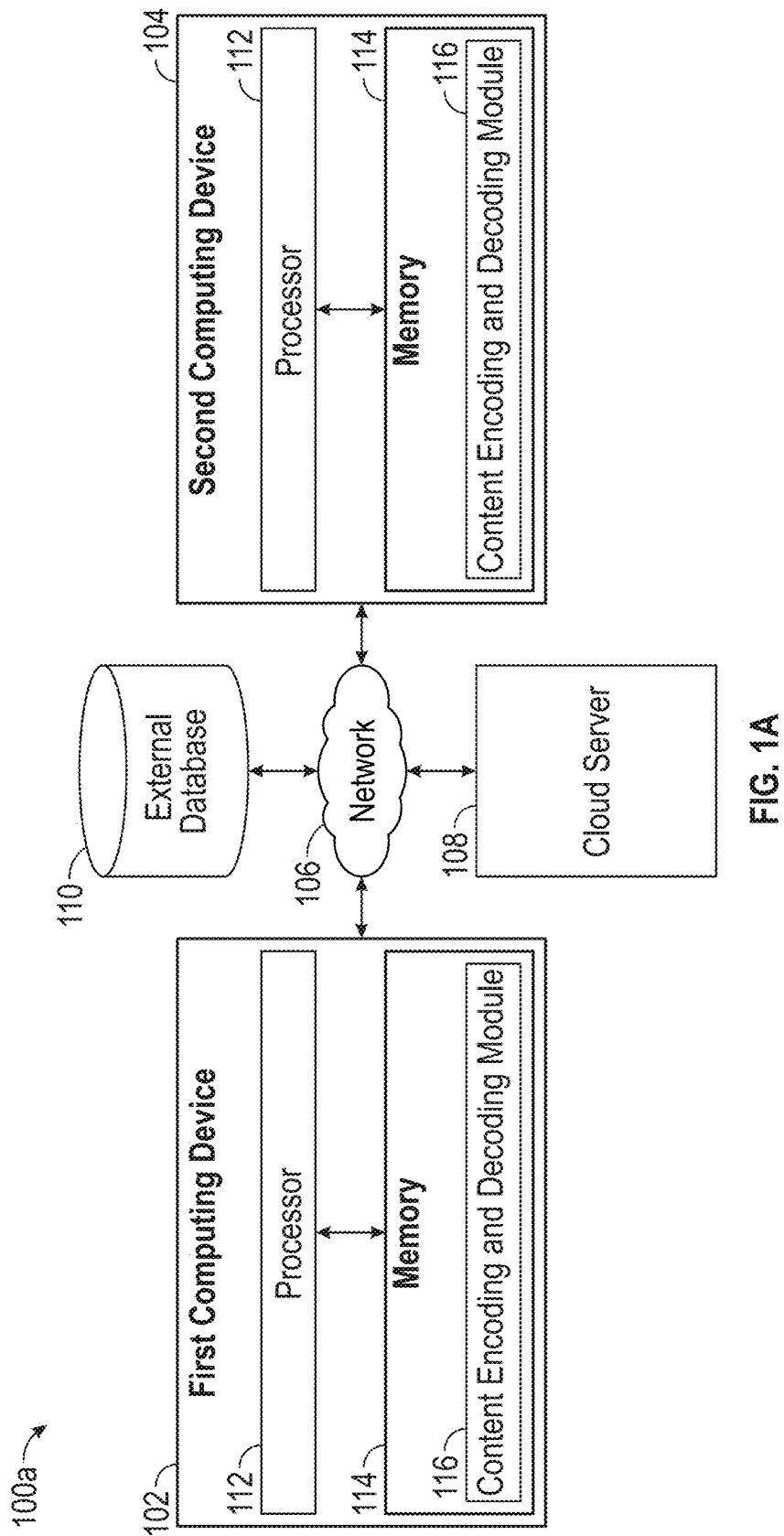
FIG. 1A is a block diagram depicting a schematic representation of a system for embedding pulse codes into content to provide secure communication, certification, and authentication in real-time, in accordance with one or more exemplary embodiments.

Furthermore, the objects and advantages of this invention will become apparent from the following description and the accompanying annexed drawings.

DETAILED DESCRIPTION OF EXAMPLE EMBODIMENTS

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and so forth, herein do not denote any order, quantity, or importance, but rather are used to distinguish one element from another.

Figure 8:
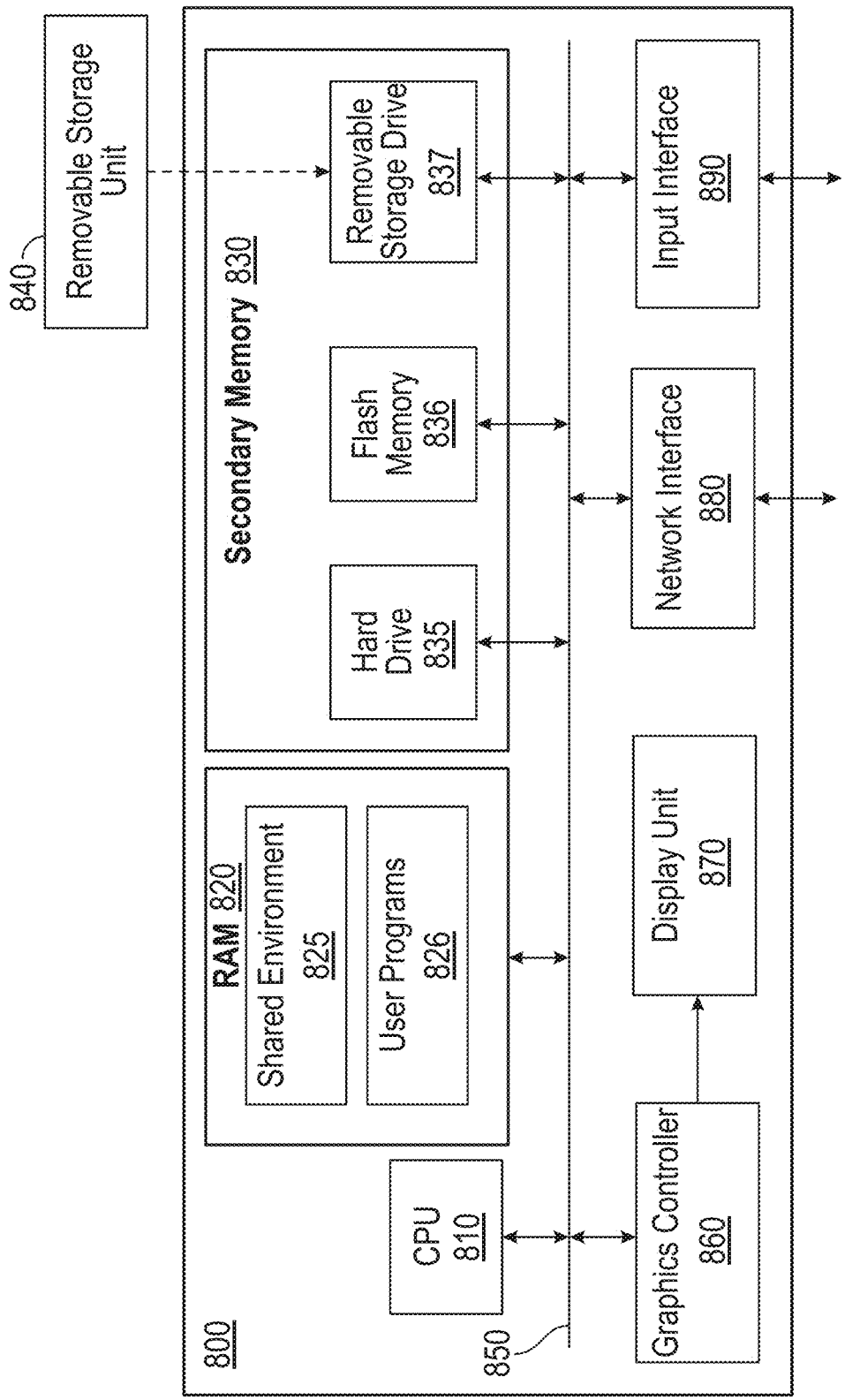
FIG. 8 is a block diagram illustrating the details of a digital processing system in which various aspects of the present disclosure are operative by execution of appropriate software instructions.

Referring to FIG. 1A is a block diagram 100a depicting a schematic representation of a system for embedding pulse codes into content to provide secure communication, certification, and authentication in real-time, in accordance with one or more exemplary embodiments. The system 100a may be a robust, dynamic, and undetectable security system/secure praxis. The system 100a includes a first computing device 102, a second computing device 104, a network 106, a cloud server 108, and an external database 110. The first computing device 102 and the second computing device 104 include a processor 112, a memory 114, and a content encoding and decoding module 116. The processor 112 includes the memory 114 may be configured to store the content encoding and decoding module 116 on the first computing device 102/second computing device 104. The processor 104 may be a central processing unit and/or a graphics processing unit (As shown in FIG. 8). The first computing device 102 or second computing device 104 may be connected to one or more computing devices over the network 106. The term "module" is used broadly herein and generally refers to a program resident in the memory of the first computing device 102 or second computing device 104.

The network 106 may include, but not limited to, an Internet of things (IoT network devices), an Ethernet, a wireless local area network (WLAN), or a wide area network (WAN), a Bluetooth low energy network, a ZigBee network, a WIFI communication network e.g., the wireless high speed internet, or a combination of networks, a cellular service such as a 4G (e.g., LTE, mobile WiMAX) or 5G cellular data service, a RFID module, a NFC module, wired cables, such as the world-wide-web based Internet, or other types of networks may include Transport Control Protocol/Internet Protocol (TCP/IP) or device addresses (e.g. network-based MAC addresses, or those provided in a proprietary networking protocol, such as Modbus TCP, or by using appropriate data feeds to obtain data from various web services, including retrieving XML data from an HTTP address, then traversing the XML for a particular node) and so forth without limiting the scope of the present disclosure. The network 106 may be configured to provide access to different types of users. The computing device 102 may include, but is not limited to, a personal digital assistant, smartphones, personal computers, a mobile station, computing tablets, a handheld device, an internet-enabled calling device, an internet-enabled calling software, a telephone, a mobile phone, a digital processing system, a virtual machine, a cloud-hosted server, a docker container and so forth. The content encoding and decoding module 116 is accessed as a mobile application, web application, and software that offers the functionality of accessing mobile applications and viewing/processing interactive pages.

The content encoding and decoding module 116 on the first computing device 102 or the second computing device 104 is accessed as a mobile application, web application, software that offers the functionality of accessing mobile applications, and viewing/processing of interactive pages, for example, are implemented in the first computing device 102 or the second computing device 104, as will be apparent to one skilled in the relevant arts by reading the disclosure provided herein. For example, the content encoding and decoding module 116 may be any suitable application downloaded from GOOGLE PLAY® (for Google Android devices), Apple Inc.'s APP STORE® (for Apple devices), or any other unified database, server, webpage, or uniform resource locator (URL). The content encoding and decoding module 116 may be a desktop application that runs on Mac OS, Microsoft Windows, Linux, or any other operating system that may be downloaded from a webpage or a CD/USB stick and the like. In some embodiments, the content encoding and decoding module 116 may be software, firmware, or hardware integrated into the first computing device 102 or the second computing device 104.

Although the first computing device 102 or second computing device 104 is shown in FIG. 1A, an embodiment of the system 100a, may support any number of computing devices. The first computing device 102 or second computing device 104 may be operated by the users or programmatically via pre-configured application logic. The first computing device 102 or second computing device 104 supported by the system 100a is realized as a computer-implemented or computer-based device having the hardware or firmware, software, and/or processing logic needed to carry out the computer-implemented methodologies described in more detail herein. The first computing device 102 may be operated by a first user. The first user may include, but is not limited to, a creator, an admin, an individual, a host, a sender, and the like. The second computing device 104 may be operated by a second user. The second user may include, but is not limited to, an authenticated user, a participant, a member, an observer, a recipient, a chat bot, pre-configured application logic, and so forth.

The system 100a intends to provide seamless real-time secure communication, certification, and authentication across a wide variety of applications by embedding a robust, dynamic, and undetectable security system/secure praxis within the content. The content may include, but is not limited to, a static piece of content, a dynamic content, a digital content and the like. The static content may include, but is not limited to, pictures, photos, images, text documents, pdf documents, word documents, executable programs, data payloads, and the like. The dynamic data may include, but is not limited to, live videos, recorded videos, sound, video conferences, interactive media, video games, and the like. The embedded pulsed content may include, but is not limited to, multidimensional data, digital objects, executables, images, video, sound, and the like. The multidimensional data may include, but is not limited to, provenance, history, time, authentication, authorship, location, device data, unique identifiers, serial numbers, encryption keys, other pulse objects, and the like. The pulse object is a multidimensional, encrypted, hidden, flexible, and dynamic data structure embedded and/or decoded into the content shared by the first user or second user in real-time and is capable of being programmatically dynamic at each sub-layer (For example, MicroPulse) of the multidimensional data and employed in a variety of use cases. The multidimensional data is undetectable and invisible to the naked eye but only visible, decodable, and authenticable by the content encoding and decoding module 116. The content encoding and decoding module 116 may be configured to perform a real-time secure multifactor authorization process into the content on the first computing device 102 or the second computing device 104.

The content encoding and decoding module 116 may be configured to embed the pulse codes into the digital content and enable the first user on the first computing device 102 to establish secure communication, certification, and authentication with the second computing device 104 over the network 106. The pulse codes may include, but are not limited to, micro pulses, PowerPulses, pulses, dynamic pulses, and the like. Secure communication may include, but is not limited to, sharing content, video conferencing, voice calling, sending texts, sending emails, posting social media content, sharing pictures, bits, bytes, and the like. The certification and authentication may include, but are not limited to, certifying, verifying the digital version of physical documents, and the like. The physical document may include, but is not limited to, passports, driver's licenses, birth certificates, vaccination certificates, and the like.

The pulse codes may include structures, multiple pulse layers, and the like. The multiple pulse layers may include, but not limited to, Pulse Capsule, Power Pulse Encryption—Key (256-bit)-The key that encrypts the data inside the Pulse, Micro Pulse—Who (i.e. user names, private keys, passwords, mac address, cookie), Micro Pulse—What (i.e. application, data type, session password), Micro Pulse—How (wireless, wireline, public wifi, LAN, WAN, VPN), Micro Pulse—Where (GPS, zip codes), Micro Pulse—Why (public, private, authentication, certification, static, dynamic), Micro Pulse—When(TimeStamps), Micro Pulse—Index(link to other databases), Micro Pulse—Logic (Parameters of Micro Pulse Interactions) (Un/Acceptable combinations of Layers,) and the like.

Figure 1B:
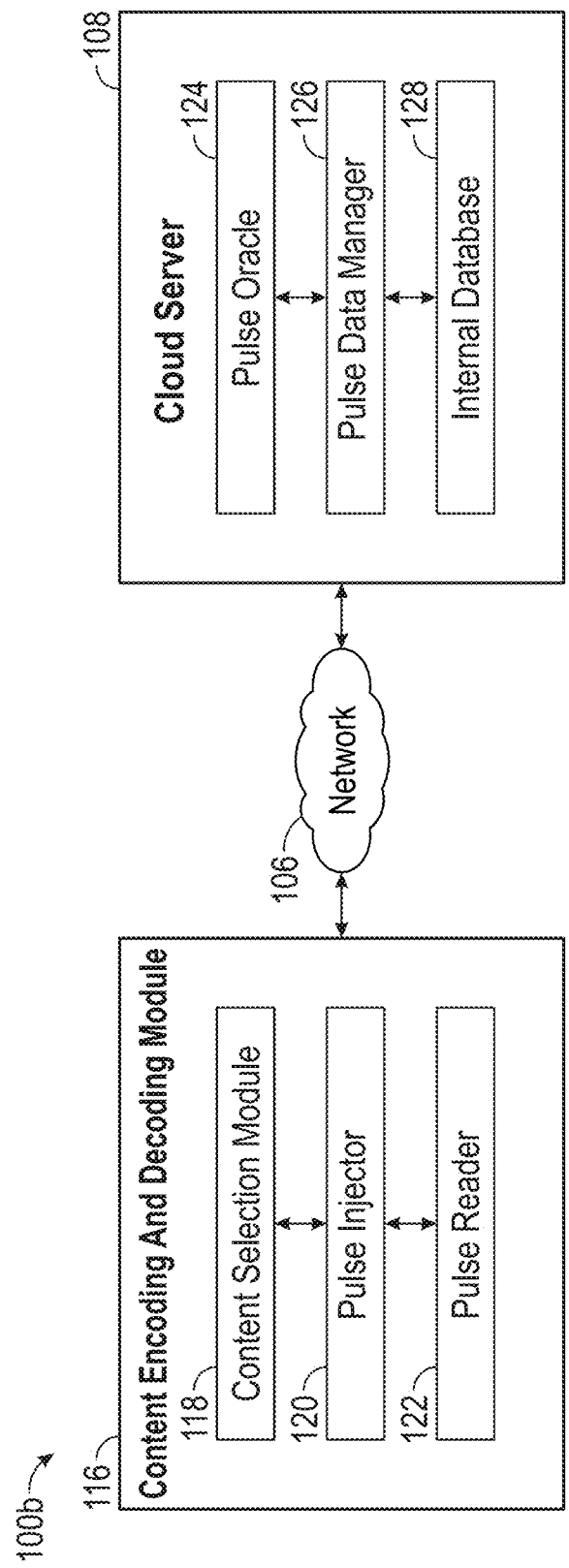
FIG. 1B is a block diagram depicting an embodiment of synchronization between the content encoding and decoding module 116 and the cloud server 108, shown in FIG. 1B, in accordance with one or more exemplary embodiments.

Referring to FIG. 1B is a block diagram 100b depicting an embodiment of synchronization between the content encoding and decoding module 116 and the cloud server 108 shown in FIG. 1B, in accordance with one or more exemplary embodiments. The block diagram 100b includes the content encoding and decoding module 116, the network 106, and the cloud server 108. The content encoding and decoding module 116 includes a content selection module 118, a dynamic pulse injector/pulse injector 120, and a pulse reader 122. The cloud server 108 includes a pulse oracle 124, a pulse data manager 126, and an internal database 128.

In accordance with one or more exemplary embodiments of the present disclosure, the content selection module 118 may be configured to enable the first user to select the content on the first computing device 102. The pulse injector 120 may be configured to inject pulse codes into the selected content in real-time. The pulse injector 120 may be synchronized with the pulse oracle 124 embedded in the cloud server 108 to programmatically and continuously change each individual pulse code and its underlying micro pulses. The pulse injector 120 includes a schema for the Pulse which is created and configured at the Pulse Oracle 124, a map of what data the specific users Pulse may consist of (which MicroPulse) layers. The pulse injector (PI) 120 may be configured to construct the pulse code structure by gathering the multidimensional data, both from the internal database 128 and the external database 110, then secures, encrypts, injects, and hides the pulse codes into the content. The pulse injector 120 may be software, and the web, embedded in an HTML browser, resides locally on a computer, cell phone, tablet, mobile device, or even within the content-generating piece of hardware directly, such as a webcam. The dynamic pulse injector 120 may be dynamically configurable, and capable of maintaining a synchronous, asynchronous, uni, or bidirectional communication with the pulse oracle 124, depending on the needs of the application.

In accordance with one or more exemplary embodiments of the present disclosure, the pulse reader 122 may be configured to read, extract, and act based on the embedded multidimensional data in the content in real-time. The pulse reader 122 is a distributed real-time software system configured to encode/decode data initiate actions and automations 100a that locates scans, and decodes the multidimensional data (For example, pulses, micro pulses) embedded into the content and creates an output based on the configuration and the content in the multidimensional data.

The configuration includes a pulse template, a Pulse Target, and the pulse reader actions for the application. A pulse administration user (oracle user) may create the new pulse template or chooses an already existing pulse template to use from the central database of the existing pulse templates while using the oracle configuration software. The pulse administration user may deploy the parameters that are to be recorded and are acceptable at the time of injection and also sets the application it may be used for (including but limited to authentication, video conference, and digital certification).

Pulse Template A: These data fields (MicroPulses) may be included in every Pulse. For example, the secret key of the first/second User, IP Address of the first/second User, session key of the group (common to all people using this application at this session), time, GPS location, and the like. The template defines which data fields need to be injected into the Pulse by the pulse injector 120. There is no limit to the types of data or number of MicroPulses that may be embedded. Even unstructured data such as voice, video, and executable apps may be embedded into the Pulse. Micro-Pulse may be interactive, configurable, programmatic, and the dynamic layers of the content, logic, apps, and functions that make up the pulse.

Pulse Target A: Threshold data values of micro pulses are allowable and make a valid pulse. The allowable threshold data values of micro pulses that make a Pulse valid may include but are not limited to the value of a Secret User Key, IP address of the first/second user must be valid compared to corporate database, valid user-inputted session key, acceptable time threshold, Must be within state that employee address has on file. The pulse target defines the only answers that are acceptable when read from the pulse by the pulse reader and may be different based on the user and their profile 122.

Now that the pulse structure (Template) and Pulse's acceptable parameters (Target) are defined, the pulse oracle 124 sends the pulse template and the pulse target to the pulse injector 120 and pulse reader 122. The pulse oracle 120 may be configured to keep the pulse injector 120 and the pulse reader 122 synchronized with correct templates and targets. This synchronization enables the pulse oracle 124 to change the structure of the Pulse dynamically and in real-time without interruption to the in-process application.

During Pulse Target configuration the first user may choose to edit or create a new pulse target. The pulse target is the set of values, for each MicroPulse that may satisfy the pulse reader 122 for authentication and certification. The values of the pulse-target may be dynamic and vary over time and the first user which makes the system very secure and flexible as it continuously monitors the context of the first user. A pulse template is selected, then an acceptable value is chosen for each MicroPulse value. The first user enters the values into the fields that may be accepted by pulse reader 122, and set the automation and information filtering restrictions.

The pulse injector 120 interfaces with the first/second user either explicitly (i.e. upload a file to Pulse) or embedded (for example, as part of video conference app) once the pulse injector 120 has received the pulse target and pulse template it is prepared to populate a pulse based on the pulse template. It fills out the information in the pulse that is specific to the user.

The pulse injector 120 sees layer 1 in the template as a secret key, so it creates layer one with User X's secret key. The pulse injector 120 sees layer two as an IP address, so it grabs User X's IP address and creates layer two with it. The pulse injector 120 continues to pull out the Pulse with information specific to User X. For example, User X pulse template A—Created Pulse secret_key_of_user_1_123ABC 192.168.1.100
session_key_value_video_conf_1
10:05:00:23
(75,-75)

The pulse injector 120 uses the information it draws from the first/second device 102 or 104. User configuration, user profile, and pulse data manager 126 may be configured to fill out the Pulse in real-time without user intervention. The pulse injector 120 may be configured to compare the pulse values to the pulse target it received from the pulse oracle 124 and halt the system and report back, or send the embedded invalid Pulse for the pulse reader to act upon.

The pulse comparison may be performed both at the point of injection by the pulse injector 120, and/or at the point of reading the Pulse by the pulse reader 122. The synchronization between the pulse injector 120 and/or the pulse reader 122 with the pulse oracle 124 may have them report the success or failure of an injection and/or reading.

The pulse comparison may be represented in the following table:

| Template Field | Template Target | Injector Value | Comparison |
|---|---|---|---|
| Secret Key of User | Valid Key | secret_key_of_user_1_123ABC | VALID |
| IP Address of User | Whitelisted | 192.168.1.100 | VALID |
| Session Key of Group | Valid Key | session_key_value_video_conf_1 | VALID |
| Time. | 10:00-11:00 | 10:05:00:23 | VALID |
| GPS Location | Home State | (75, −75) | VALID |

The pulse reader 122 is configured to perform a synchronous, asynchronous, and uni or bidirectional communication with the pulse oracle 124. The pulse oracle 124 may be configured and synchronized with the pulse reader 122 and sets its instructions on how to handle MicroPulse decode and what application, technical, or operational steps to take depending on the pulse data received and the application being used. The configuration of the pulse reader 122 may be dynamic, static, or conditional based on the application needs and the use case of the pulse platform.

The pulse reader 122 is synchronized with the pulse oracle 124 and informs the status of Pulse decoding to the pulse oracle 124. Incorrect/unauthorized Pulses and the offending MicroPulses may be analyzed by the pulse oracle 124 for forensic analysis. The pulse reader 122 may be configured to decode the Pulse and MicroPulse Data, extract additional data from the data sources/databases (both internal database 128 and the external database 110), and then deliver data to the first computing device 102/the second computing device 104 (user interface) for real-time reporting/dashboarding, or is able to trigger another application, action or logic sequence that may be dynamic based on the data inside the Pulse. The actions performed by the pulse reader 122 may be read from the multidimensional data itself or configured in the platform by the pulse oracle 124. The pulse reader ingests content, identifies if there is a pulse embedded in it, aggregates all needed data for the configured application, and then performs actions based on the application and the profile of the user. The pulse reader 122 may act as a standalone application on the phone or in the cloud but also may be embedded directly into an application and be invisible to the user. The pulse reader 122 must remain synchronized with the pulse oracle 124, as it must know the structure of the pulses to look for.

The pulse reader 122 may be configured to obtain pulse template and pulse target from pulse oracle 124. The actions performed by the pulse reader 122 may include, but are not limited to, application user, user X may login to application, the pulse reader determines what level of information user X is allowed to see, or what specific actions to perform, or what actions they have access to base on their profile, content is ingested, Pulse is located, Pulse is decrypted, Pulse values are compared to Pulse Target, Pulse is certified as acceptable or Not, the pulse reader 122 informs the pulse oracle 124 of success or failure, the pulse reader may be configured to perform function appropriate to successful or failed Pulse. The success may include authenticating and staying on a conference call and the like; the failure may include, being removed from a conference call and the like.

Examples of actions include a company emails identically looking coupons to 1000 existing customers, each with a unique code pulsed in it, invisible to the user. The instructions say, "Text this coupon to number 555-555-5555 for 50% off!". The first user or the customer who texts the unique code pulsed to the number 555-555-5555 receives a discount. However, the first user may be able to post the coupon on his social media because it's such a great deal, and it's downloaded by 100 of his followers. The pulse reader 122 ingests the picture from the SMS application and checks for a valid pulse. If the Pulse is valid, and the sending phone number matches the customer profile the pulse reader 122 activates the shopping cart with a 50% discount. The first user/customer receives a responding text with a link directly to this shopping cart.

When the second individual (a follower of the first user) sends the coupon to the same number, the system sees the first user has already used this coupon and that it is coming from a number that is not the first user and not in its customer database. The pulse reader 122 is configured to take a different action. One example might be to send a text response that says, "Sorry, this coupon has been used!" Another action might be to direct the second user to sign up as a customer and then give her the same discount. The system can also track how many new customers are generated using the first user coupon and add that information to his customer profile A similar example could be used to prevent Phishing exploits.

Changing actions based on the user reading the Pulse: If there is a database embedded in the pulse reader 122, the pulse reader 122 delivers only information that the first user is able to view. A decision maker may be allowed to view all of the data when the first user uploads the pulsed document to the pulse reader 122, but an administrative assistant may only be able to see who wrote it and when. Department heads may only be able to see the data related to their departments.

Other pulse reader actions may include changing output or action based on data feeds in pulse data manager 126, displaying different output based on the user's location, displaying different output based on current weather at the user's location, and displaying the geo-locations that need maintenance within ten miles and is color-coded by severity.

In accordance with one or more exemplary embodiments of the present disclosure, the cloud server 108 includes the pulse oracle 124 may be a high-level software management system and is configured to enable programmatic, dynamic, and real-time configuration, synchronization, and management of the pulse injector 120, and the pulse reader 122. The pulse oracle 124 may be the main configuration and provisioning system for the content encoding and decoding module 116. The pulse oracle 124 may be configured to enable the creation of pulse templates and the declaration of acceptable thresholds of the content for each MicroPulse (Pulse Target). The pulse oracle 124 may be configured to distribute the pulse template and pulse targets to the other components of the pulse data manager 126, and the pulse oracle 124 may be configured to monitor the payload of rejected payloads.

An organization with titles, regions, departments, and roles may impose the same informational organization on the system. The pulse data manager 126 may act as an interface between the pulse platform and the existing internal data of a company, and pulse users can be mapped to their corresponding domains in their organization. The pulse data manager 126 may act as an API manager that prepares, processes, and provisions data for configuring pulse templates and pulse targets.

In order for each micro Pulse to be filled correctly at the point of injection, the injector must have access to the multidimensional data to fill out each field. Some layers may come from the first/second computing device itself (For example, GPS, MAC Address), which the injector may capture directly, but some may come from other databases (External Database). The pulse data manager 126 may be configured to map these outside data sources and organizes them for efficient use in creating pulse templates, filling out pulse data fields, and facilitating pulse comparisons, pulse reader output, and actions. The pulse data manager 126 may also be configured to combine multiple data sources and perform data transformations and calculations in order to create the data type and data value that is required by the pulse template.

The other sub-components of the pulse data manager 126 may include a data-aggregator and a data transformer. Each pulse data feed is defined as the data (in full or in part) needed to populate a MicroPulse layer. The data aggregator is used to map data feeds from outside external source schemas to a normalized internal PowerPulse schema. The data aggregator manages the frequency of the source data feeds and maps the source time series onto the time series needed for the pulse code. The pulse data transformer may combine, aggregate, and transform data from multiple feeds to engineer a feed needed for the pulse code or for an output action needed.

The examples of aggregator may include, but is not limited to:
  Data in: Stock price feeds every minute a Data Out: end of day price
  Data in: Hourly wind velocity in a zip code a Data Out: Wind max for the day
  Data in: All hashed passwords used by a user a Data Out: current hash
  Data in: Number of concurrent website users hourly a Data Out: current website users
  Data in: Daily number of new customers a Data Out: new users for the month The examples of data transformers may include, but are not limited to:
  Data in: daily rainfall by zip code
  Data in: daily temperature in Fahrenheit
  Data in: Longitude, Latitude
  Data Out: Average Monthly Temperature, in Celsius, in the county user is in Once the aggregator and transformers data values are set, the aggregator and transformer may autonomously fetch, groom and transform the incoming data to the needed data structure and data values for use by the system.

For example, the pulse oracle 124 is configured to change the pulse template and/or pulse target dynamically in real-time to strengthen the security and make brute force attacks more difficult when an intrusion is suspected or an anomaly is detected. The secure connection may lose all progress and need to start from ground zero if any unauthorized user (party) attempting to brute force during the communication between the first computing device 102 and the second computing device 104, in which the pulse oracle 124 may react continuously by changing the pulse structure and target values of the multidimensional data. Depending on the application, and safety requirements, dynamic multidimensional data may be designed from the beginning. The pulse oracle 124 may be configured to retain the pulse reader 122 and the pulse injector 120 and are synchronized for safety requirements.

The pulse oracle 124 may also be configured to manage the provisioning of the multidimensional data from the internal database 128 and the external database 110 and synchronizes the multidimensional data availability with the first user/enterprise provisioning. Multiple users may view the multidimensional data they are entitled to see as per user-profiles and roles. The pulse oracle 124 may also be configured to enable the first user/second user to set the pulse structure and pulse target but not necessarily see the multidimensional data that populates those fields, which allows greater data security. It would be extremely difficult for an intruder to hack a connection protected by a pulse that included a continuously changing high-bit private key, and a dynamic single use session key, that is changed on every missed attempt.

In accordance with one or more exemplary embodiments of the present disclosure, the pulse data manager (PDM) 126 may act as an intermediary and staging area for all data types delivering multidimensional data to the pulse oracle 124 and other components of the system in real-time. There are multiple ways to transfer data (protocols) and just as multiple data formats (schemas). The pulse data manager 126 may be configured to access the needed feeds via any protocol and be able to decode any type of schema, including the ability to send executable applications, video, and images as a data feed. Protocols that can be utilized may include, but are not limited to, HTTP, HTTPS, WebSockets, SOAP, REST, IP, TCP, SMTP, POPS, UDP, RDP, DNS, SIP, SMB, SNMP, SSH, Telnet, VNC, ARP, Blockchain, Non-fungible tokens, Digital Tokens, and the like.

Schemas are how the data is organized and stored as it is transmitted and often must be converted from how it is organized at the source to how it will be used by the platform. The pulse data manager 126 may be configured to decode the source data and map the data to the schema needed by the system. Once the initial configuration and mapping are performed, the pulse data manager 126 may continuously keep all data feeds ready to support existing pulse needs. The pulse data manager 126 has the ability to ingest multiple data types and schemas, including Excel, CSV, SQL, NOSQL, JSON, Pickles, Bytes Objects, String Objects, binaries, raw bits, arrays, dictionaries, data maps, Images, Videos, and the like.

Application logic and transformations may occur in the pulse data manager 126 to engineer the data features that are needed to embed into the multidimensional data as well as to perform any logical comparisons, calculations, and transformations that are needed for reporting, application-export, and other actions. It also acts as a firewall for data leakage and data isolation.

The data features are high-value data items that are created when raw data from one or multiple sources is combined, aggregated and/or transformed to provide a custom application and user-specific piece of usable information. A list of all wildfires in the country, their direction and speed of travel, combined with a person's location, and the weather outlook may be combined and transformed to give a user a wildfire 24 hr risk probability.

The data features are engineered from multiple data sources to provide custom specific data relevant to the user, the Pulse, and the specific application. The formula for fetching the raw data needed, decoding it, and transforming it into the data feature series needed by the system allows this to be done automatically, programmatically, and transparently to the users.

The pulse data manager 126 may represent the multidimensional data that resides outside the pulse system. The system pulls in this multidimensional data for multiple uses. The internal database 128 may be configured to represent the internal data of a company, enterprise, or organization. Users of the pulse system may include multidimensional data from those internal systems as part of the pulse system. In fact, the pulse system is used to protect that multidimensional data and ensure it is only used by authorized individuals.

Company 'A' may be able to restrict the information able to be viewed by the user based on user roles and defined in its own system. The CEO of a Computer Company may be able to view all of the information in pulsed documents except Human Resource data because his pulse profile is linked to his Computer Company user profile. Only Human Resource executives in Computer companies may be able to read personnel-related pulsed documents because they are also linked.

The external database 110 represents any, and all outside data feeds that may be relevant or needed for filling out MicroPulse fields, authenticating MicroPulse fields, or creating data features needed for pulse creation, comparison, or output actions to be undertaken by the pulse reader 122. Examples of outside data feeds can include but are not limited to, social media feeds, weather feeds, stock feeds, product and service reviews, location based services, news feeds, event feeds, product data, classified feeds, IoT feeds, customer feeds, supplier feeds and the like.

In accordance with one or more exemplary embodiments of the present disclosure, to certify authenticity, a pulse structure is injected into a digital asset/content (For example, a picture, document, or video) by the first user to certify authorship and prove authenticity. The pulse reader 122 may be configured to resolve the dispute by decoding the pulse structure injected into the content when another party distributes the asset or claims the authorship.

In accordance with one or more exemplary embodiments of the present disclosure, to certify dynamic authentication in the content and communications that occur over a time series (For example, video conference, video call, voice recording, song recording, and digital video), a pulse that is dynamic in nature may be injected into every frame and change over time. Parameters may be set at the MicroPulse level that each participant must follow to be authenticated. For example, in one use case, if the user's GPS location must be within a certain area and coming from the first/second computing device 102 or 104 with an approved IP and/or MAC address. The dynamic authentication is managed at the pulse oracle 124.

In accordance with one or more exemplary embodiments of the present disclosure, smart contract wrapper around traditional contracts, embedding data directly into a Non-Fungible Token (NFT) to verify the actual media (picture or video's) authenticity. The synchronization between the pulse reader 122, pulse oracle 124, and pulse injector 120 may dynamically change the accepted values in real-time, forcing the unauthorized user to start at ground zero each time when a layer fails to authenticate (does not provide a pulse that is deemed as authentic). Each micro Pulse is a hashed (encrypted) value asserted against a set of approved data values (and logic) managed by the pulse oracle 124. The pulse oracle 124 may programmatically change each individual security component in real-time. By changing the pulse structure of each individual security component (multidimensional data) in real time dramatically reduces the efficacy of brute force techniques as every wrong answer attempts to be guessed.

Each pulse may have a type of data that it is associated with, the applications may be varied and either be static (documents, or images) or dynamic(i.e. video audio, or communications). The system 100a, and 100b represents the creation and administration of the applications embedding the pulse into the content.

Figure 2:
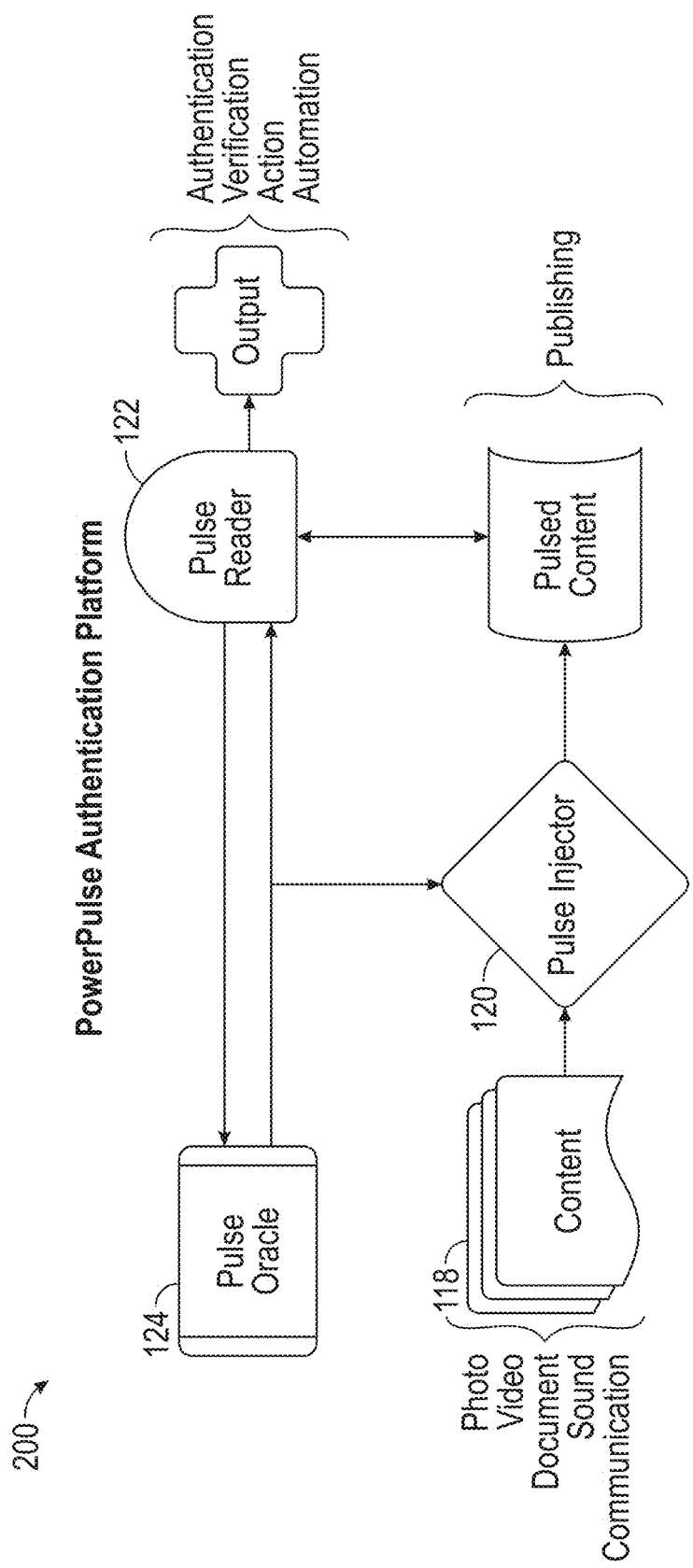
FIG. 2 is a block diagram depicting an embodiment of the pulse code encoding flow, in accordance with one or more exemplary embodiments.

Referring to FIG. 2 is a block diagram 200 depicting an embodiment of the pulse code encoding flow, in accordance with one or more exemplary embodiments. The block diagram 200 includes the content selection module 118, the pulse injector 120, the pulse reader 122, the pulse oracle 124, and the pulse data manager 126. The content selection module 118 may be configured to enable the first user to select the content/or communication to protect.

The pulse injector 120 may be configured to select pulse configuration from the pulse oracle 124 based on the application selected by the first user to use it in, or the pulse injector 120 may be configured to enable the first user to hardcode a specific pulse for a specific use-case. The pulse oracle 124 may be configured to arrange acceptable thresholds for each MicroPulse (layer) that satisfies a valid Pulse.

For example, embedding the micro pulses for a secure Video Conference

MicroPulse 1: Password is correct for the user

MicroPulse 2: Location must be within a given area (that can vary per person) user A must be in the office in a first location, and User B must be at a factory in a second location.

MicroPulse 3: Users may only join within ten minutes of the scheduled start time; this can be user-specific, so it can be updated in real-time if someone is late or removed for a VIP such as a CEO MicroPulse 4: The IP address must be on a list of acceptable IP addresses unique per person (whitelisted).

The pulse oracle 124 may be configured to create the pulse structure by configuring application and/or content-specific layers upon selecting the content on the first computing device 102/the second computing device 104. The MicroPulse layers may be embedded into each individual multidimensional data of the content. Each individual micro pulse layer may define the input and derive the multidimensional data programmatically (For example, Password vs. current GPS Coordinates). Each individual micro pulse layer may be named, defined, and saved in the internal database 128 and the external database 110 for later use, so a wide variety of pulse types may exist for different applications. These pulses may be embedded in real-time into the content to be secured.

For example, each individual micro pulse layer may include,

MicroPulse (layer) Layer 1—User Input: secret key
MicroPulse (layer) Layer 2—Programmatic: Current GPS Coordinates
MicroPulse (layer) Layer 3—Programmatic: Timestamp
MicroPulse (layer) Layer 4—Programmatic: IP Address In another example, the content encoding and decoding module 116 is configured to handle the N number of MicroPulses into the content to be secured.

The pulse oracle 124 may be configured to load the pulse configuration and create the user-specific pulse object (pulse structure) and encrypt, embed, and hide the pulse code into the content in real-time. The pulse code may be generated once for the static content or may generate multiple times for dynamic content. The pulse oracle 124 may be configured to inform the first user if the requirements are not met (depending on security needs) at onset or enable the pulse oracle 124 to mark as failed, reporting these attempts to the pulse oracle 124 depending on the security needs.

For example, the first user is notified if the wrong Password is entered by an unauthorized user/intruder. The first user may realize and notice the anomalies when the unauthorized user tries to gain access to the conference outside the time window or from an unauthorized location security.

Once a successful pulse code is assigned, and injected into the content, then the content may reside encrypted and hidden using various techniques depending on the content type. If the content is dynamic such as a video conference or video, the pulse injector 120 may be configured to inject pulse codes at regular intervals throughout the content (one to many times per second), and therefore, the content is more dynamic and secure as pulse values may change frequently and move throughout the duration of the dynamic content.

For example, a video conference may include a 'session' key as a MicroPulse that changes every one minute that shuts down the system if the session key is deemed not valid.

The pulse oracle 124 and the pulse reader 122 are synchronized to verify that each pulse code is authentic and the multidimensional data varied within the Pulse (Each MicroPulse Layer) still meets the configured criteria. If the pulse code is not valid at any point because one or more of its layers are no longer acceptable, the pulse reader 122 may notify the pulse oracle 124, and the pulse injector 120 may cease. This may go on for the entire duration of the dynamic content.

For example, if a participant on the call is driving and changes a location with respect to an allowable GPS threshold, the participant pulse code becomes invalid (GPS MicroPulse no longer valid) and drops the participant from the call. The pulse oracle 124 may be notified of the changed location and the track record of the changing GPS pulse values.

The pulse reader 122 may be configured to decode the pulse information from the content and provides output information, programmatically initiates other logic and actions, or certifies authenticity. The pulse reader 122 may be configured to read, unhide, and decode the information/objects/content embedded in the pulse codes. This can be used for authentication of access across multiple different axes or for the certification of authorship or acceptance. Even a traditional signed paper document may include a pulse code created and configured in order to act as a smart contract with an agreed-upon scan/picture/PDF acting as the content.

For example, collaborators (For example, editors, special effects, colorists, sound engineers) on the media creation may include pulsed work so that in the event a movie gets stolen, the version can be traced back to the point of theft.

In another example, a digital coupon may be distributed by a company to customers and appear the same to all the customers, but the coupon embeds information about a particular customer and how the coupon is specifically sent to or acquired by the customer; therefore, the company can use this to limit the coupon use or to provide loyalty awards to the original customer for referring new customers.

In another example, a standard digital image, once pulsed by an authenticated user, acts as a certified digital version of a physical document. A vaccine card may be authenticated, then a picture of the vaccine card is pulsed so the pulse reader may prove the vaccine card is authentic; the same method may be used for Passports, Drivers Licenses, Birth Certificates, and so forth. Further, the picture of the card may be used to fill out the forms automatically because all of the data can be embedded within the physical document.

In accordance with one or more exemplary embodiments of the present disclosure, a video conference participant cannot join if the correct Pulse is not detected within the video conference stream coming from the participant. The pulse code is generated if the security elements (MicroPulses) have been satisfied. The correct pulse code is unique to each participant and must remain throughout the entire duration of the video conference in order to continue the communication. So the security measures must be present not just at the outset of the video conference but during the entire duration of the video conference. Further, a new pulse code and certain MicroPulse layers are automatically generated. They are now required by all active participants when a certain threshold of pulse codes is incorrect or absent. This is managed by the oracle and will be transparent to users who are correctly authenticated, however, any unauthorized brute force hacking attempts must start over at ground zero.

In accordance with one or more exemplary embodiments of the present disclosure, the use of MicroPulse layers as a method for determining cyber-attack origination. If the pulse reader 122 detects an unauthorized attempt to authenticate the content, the pulse reader 122 may be configured to use the MicroPulses(layer) data supplied in order to identify the bad actor and other forensic information about the nature of the attack.

For example, a person tries to authenticate to a video call by social-engineering the login credentials of a participant (Participant A). Once the video stream begins, the pulse injector 120 is configured to embed Data MicroPulses (Data includes GPS location, IP address, browser type, etc.) and is not compatible with the authentication of the system and flags the content by the pulse reader 122. The pulse reader 122 may be configured to report the unauthorized pulse codes and track the information being sent to help identify the intrusion. The system identifies when someone is attempting to impersonate Participant A, generates a new set of credentials, and/or forces a password reset, and iterates session keys automatically and dynamically to eliminate brute-force progress by the attacker, but still enabling the authorized user to attend the meeting. Embedding the pulse codes (multidimensional data) within the content of the video frame enables privacy and security across multiple different axes. Artificial Intelligence models can count the number of people in the video stream, and embed the data in the Pulse, thereby dropping the video call if a face is not known, or there are multiple people in the frame.

Computer vision, artificial intelligence, machine learning, and Transformers process the frame and deliver real-time inference data to embed into the video frame itself for data logic, automation, authentication, and certification in real-time. If the data embedded in the Pulse does not match the configured allowed Pulse, the user could be dropped.

In accordance with one or more exemplary embodiments of the present disclosure, a company has a pulse configured, so invited video conference call participants must be authenticated and alone during the video call. In each Pulse, a real-time object detection algorithm matches the face of the participant to a ground truth photo and counts the total number of faces for each user. If the face is not a recognition match, the call drops; if there are multiple faces in the feed, the call drops. If a spouse walked into the camera range or a passer walked by in the background, the connection would be halted until the connection is reconciled. This is an example of how the pulse code could be used to dynamically make sure only those who are specifically invited and continuously authenticated can participate.

This is one example of how hundreds of artificial intelligence, and machine learning models could synchronize with this dynamic, complex system. All authentic texts/emails could have a pulse attached to the content that authenticates that the communication is from the stated sender and meant for the recipient, greatly reducing phishing.

In accordance with one or more exemplary embodiments of the present disclosure, embed data in a broadcast: Broadcast networks could embed large amounts of real-time streaming data into their video feeds. Home shopping channels could embed data about the products or offer unique deals to each person watching based on their customer loyalty status. Sports could embed the statistics directly into the broadcast feed.

In accordance with one or more exemplary embodiments of the present disclosure, embed pulse codes in the social media posts: a pulse code could be embedded into social-media posts/pictures/videos that would allow users to more easily download and share that content while retaining data inside the content about which user downloaded it, which posted it, so its use can be easily tracked and certified.

A simple digital coupon could have a pulse embedded in it that may enable a company to track its usage, including who it was sent to, who it was forwarded to, and the entire history.

In accordance with one or more exemplary embodiments of the present disclosure, a video streaming platform could use Pulse to stop its customers from sharing passwords. Broadcast binary distribution—Hyper efficient distribution of software. A broadcast technique could be used to encode files, media, applications, data, and the like, into the video stream itself, utilizing a single stream of bandwidth to send millions of people an application or set of applications for the bandwidth cost of one.

Broadcast downloading: Non-interactive TV channels can deliver their own client software via the broadcast to become interactive. Embed a unique ID into a digital image, that image once passed to the pulse reader for delivering all the information attached to that unique ID.

All of the information does not need to be embedded directly in the content. Instead, unique ids can be used as a key to system data that can be delivered based on different roles and security needs. For example, an anonymous patient ID number may be embedded into a picture of an infectious test result; the doctor will receive all available personal and health information when the patient ID number is read by the pulse reader, thereby enabling the doctor to append to an electronic medical record.

If an airline received that picture of the infectious test result with the embedded data to use for safety screening, they would be only be authorized to see the negative results of the test and enabling the passengers to get onto the plane without compromising the health data.

Figure 3:
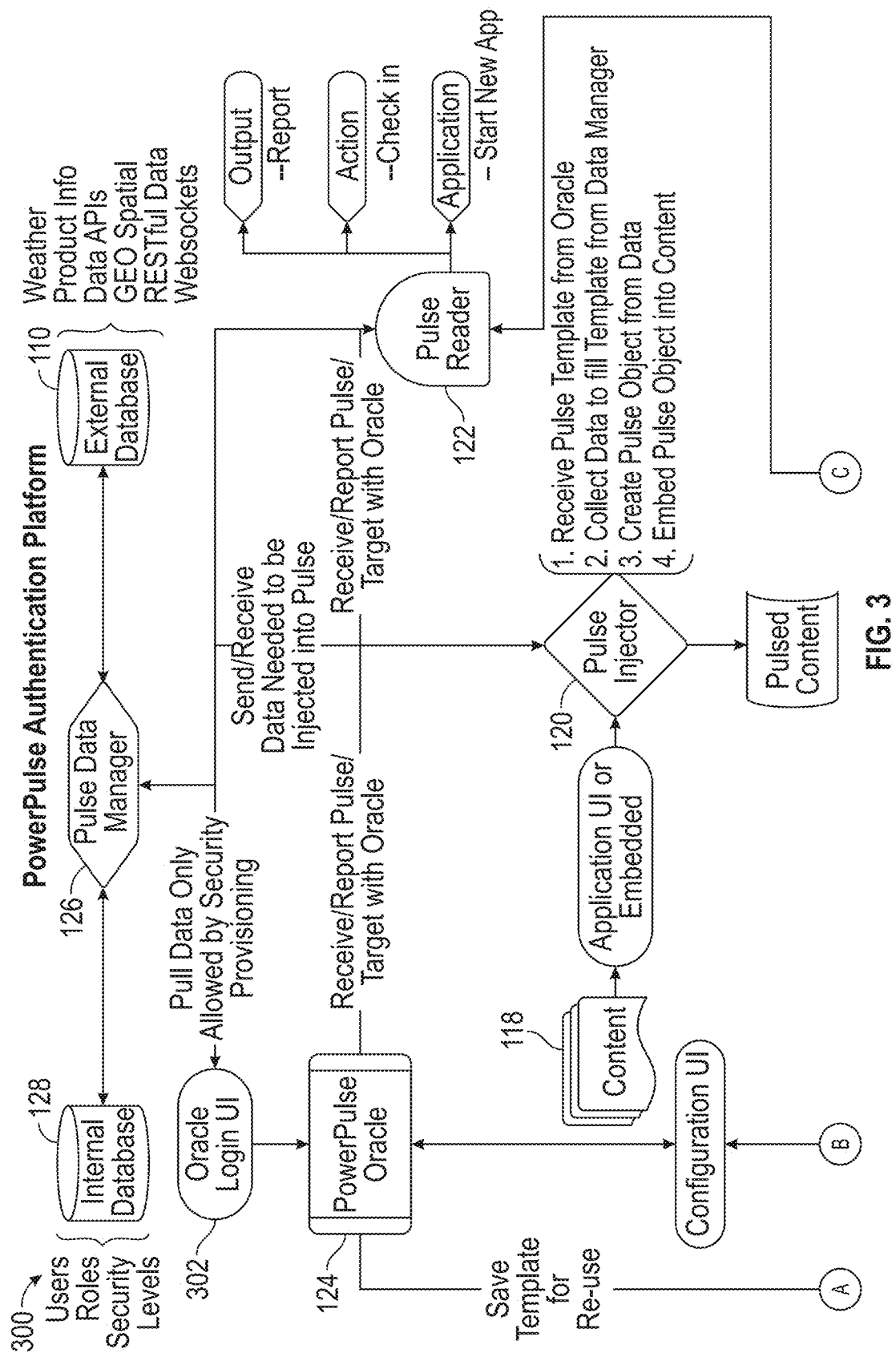
FIG. 3 is a flow diagram depicting another exemplary embodiment for embedding multidimensional data into the content in real-time, in accordance with one or more exemplary embodiments.
Figure 3:
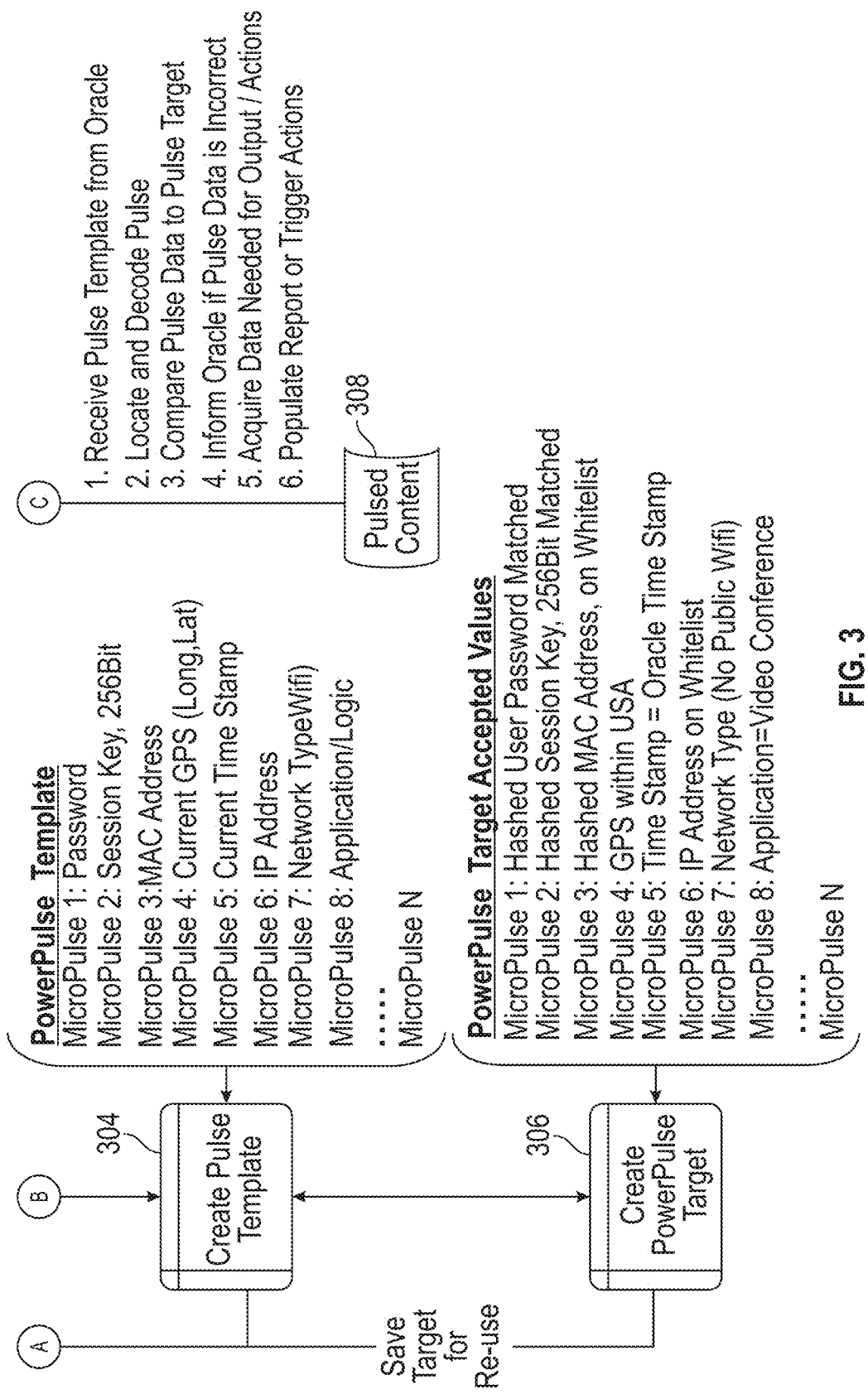

Referring to FIG. 3 is a flow diagram 300 depicting another exemplary embodiment for embedding multidimensional data into the content in real-time, in accordance with one or more exemplary embodiments. The flow diagram 300 may be carried out in the context of the details of FIG. 1A, FIG. 1B, and FIG. 2. However, flow diagram 300 may also be carried out in any desired environment. Further, the aforementioned definitions may equally apply to the description below.

The flow diagram 300 includes an oracle login user interface 302, a pulse template 304, a pulse target 306, the content selection module 118, the pulse injector 120, the pulse reader 122, the pulse oracle 124, and the pulse data manager 126. The oracle login user interface 302 may be configured to pull data allowed by security provisioning. The pulse oracle 124 may be configured to save the pulse template 304 and the pulse target 306 for re-use. The pulse template 304 may be configured to save any number of configurations with such examples as: MicroPulse 1: Password, MicroPulse 2: Session Key, 256 Bit, MicroPulse 3:MAC Address, MicroPulse 4: Current GPS (Long, Lat), MicroPulse 5: Current Time Stamp, MicroPulse 6: IP Address, MicroPulse 7: Network TypeWifi), MicroPulse 8: Application/Logic, . . . MicroPulse N. The pulse target 306 may be configured to show all of the acceptable values for each Micropulse (these are example answers): MicroPulse 1: Hashed User Password Matched, MicroPulse 2: Hashed Session Key, 256 Bit Matched, MicroPulse 3: Hashed MAC Address, on Whitelist, MicroPulse 4: GPS within USA, MicroPulse 5: Time Stamp=Oracle Time Stamp, MicroPulse 6: IP Address on Whitelist, MicroPulse 7: Network Type (No Public Wifi), MicroPulse 8: Application=Video Conference, . . . MicroPulse N.

The MicroPulse configuration of the pulse oracle 124 enables the first user to define the individual fields that may be incorporated into pulses for authentication and certification in real-time. Once created here, they will be listed for inclusion into a MicroPulse, and then listed for a target value in the Pulse target.

The pulsed content 308 may be configured to receive pulse template 304 from the pulse oracle 124, locate and decode Pulse, compare pulse data to pulse target 306, inform the pulse oracle 124 if pulse data is incorrect, acquire data needed for output/actions, populate report or trigger actions.

The pulse injector 120 may be configured to receive pulse template 304 from the pulse oracle 124, create pulse object from the multidimensional data, collect multidimensional data to fill template from the pulse data manager 126, and embed pulse object/code into the content.

The pulse reader 122 is used to decode the pulse information from the content and can output the information, programmatically initiates other logic and actions, or certify authenticity. The pulse reader 122 may be configured to read, unhide, and unencrypt the information/objects/content embedded in the pulse codes. This can be used for authentication of access across multiple different axes or for the certification of authorship or acceptance. Even a traditional signed paper document may have a pulse code created and configured in order to act as a smart contract with an agreed-upon scan/picture/PDF acting as the content.

The pulse data manager (PDM) 126 may act as an intermediary and staging area for all data types delivering multidimensional data to the pulse oracle 124 and other components of the system in real-time. Application logic and transformations may occur in the pulse data manager 126 to engineer the data features that are needed to embed into the multidimensional data as well as to perform any logical comparisons, calculations, and transformations that are needed for reporting, application-export, and other actions. It also acts as a firewall for data leakage and data isolation.

The internal database 128 may be configured to store user profiles, roles, security levels, and the like; it represents internal data sources to a user. The external database 110 may be configured to store weather, product information, data APIs, GEO spatial, RESTful data, web sockets, and the like; it represents data sources outside the user organization.

Figure 4A:
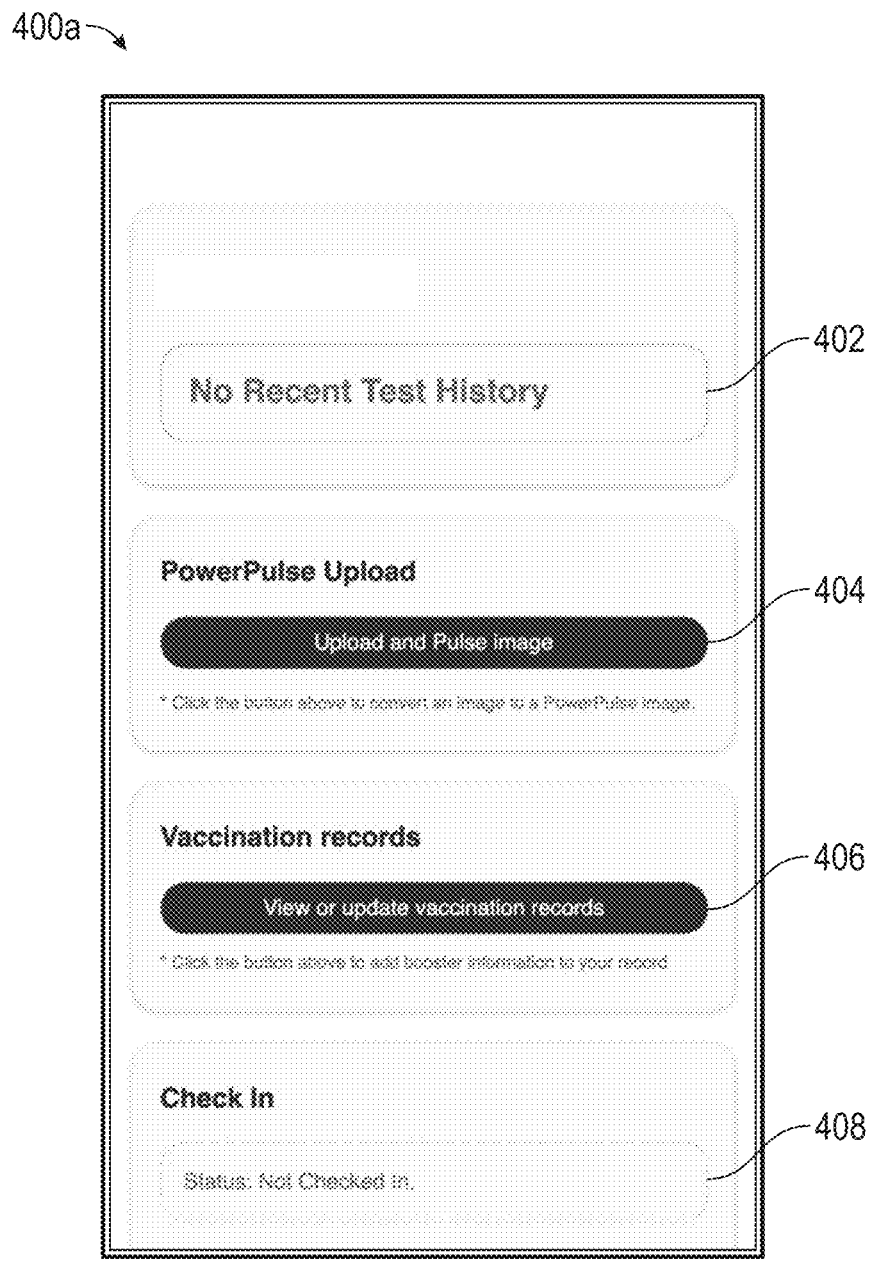
Referring to FIG. 4A is an example screen depicting an embodiment of encoding the content by the content encoding and decoding module, in accordance with one or more exemplary embodiments.

Referring to FIG. 4A is an example screen 400*a* depicting an embodiment of encoding the content by the content encoding and decoding module, in accordance with one or more exemplary embodiments. The example screen 400*a* depicts no recent test history option 402, an upload and Pulse image option 404, view or update vaccination records option 406, and a check-in option 408. The no recent test history option 402 may be configured to enable the first user or the second user to review the recent history of the content selected from the first computing device 102 or the second computing device 104. The upload and pulse image option 404 may be configured to enable the first user or the second user to convert the content into the pulsed content by embedding pulse codes within the content. The view or update vaccination records option 406 may be configured to enable the first user or the second user to review the pulsed vaccination records and add the booster dose information to the first or second user records. The check-in option 408 may be configured to enable the first user and the second user to check the status of the uploaded content.

Figure 4B:
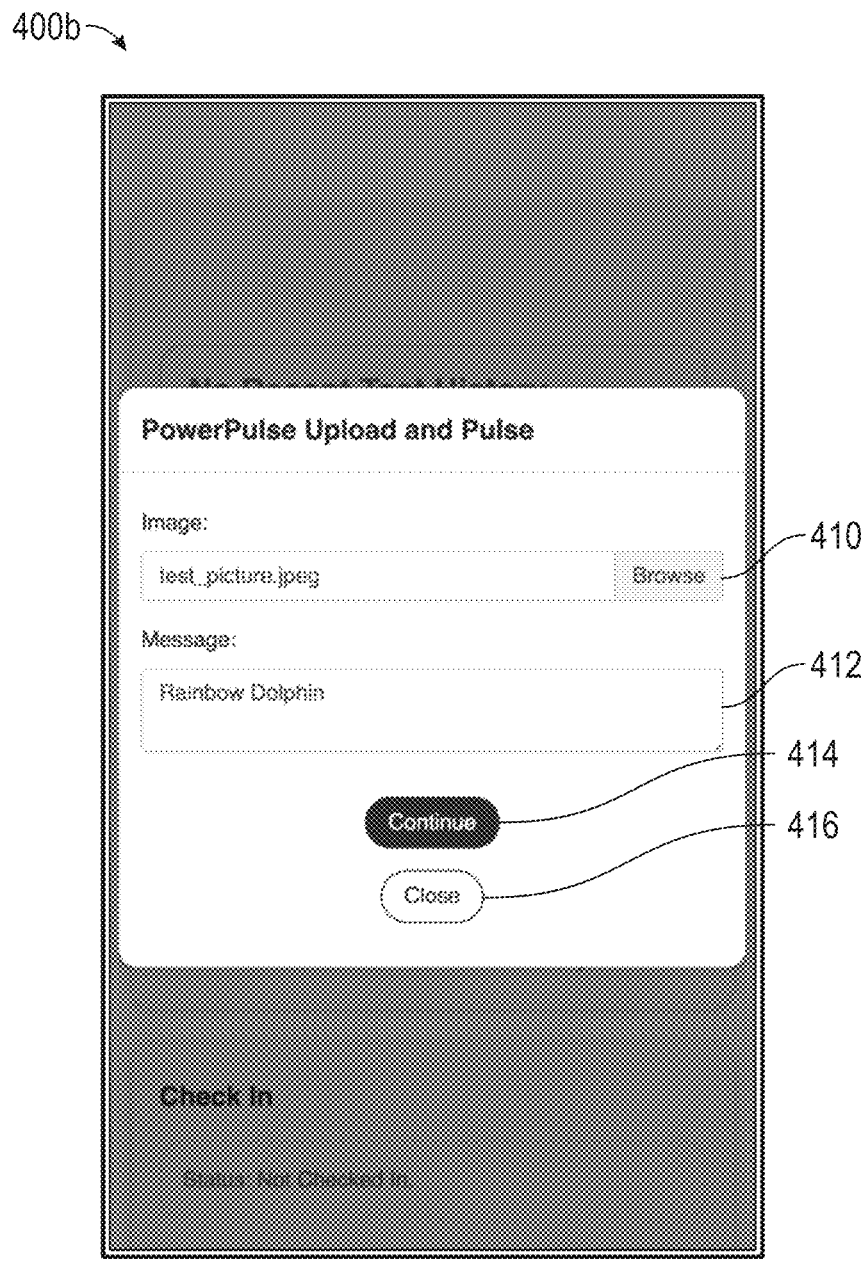
FIG. 4B is another example screen depicting another embodiment of encoding the content by the content encoding and decoding module, in accordance with one or more exemplary embodiments.

Referring to FIG. 4B is another example screen 400*b* depicting another embodiment of encoding the content by the content encoding and decoding module, in accordance with one or more exemplary embodiments. The screen 400*b* depicts a browse option 410, a message option 412, the close option 414, and a continue option 416. The browse option 410 may be configured to enable the first user or the second user to browse the content to upload on the first computing device 102 or the second computing device 104. The message option 412 may be configured to enable the first user or the second user to add a message along with the content to post on the first computing device 102 or the second computing device 104. The close option 414 may redirect to the home page.

Figure 4C:
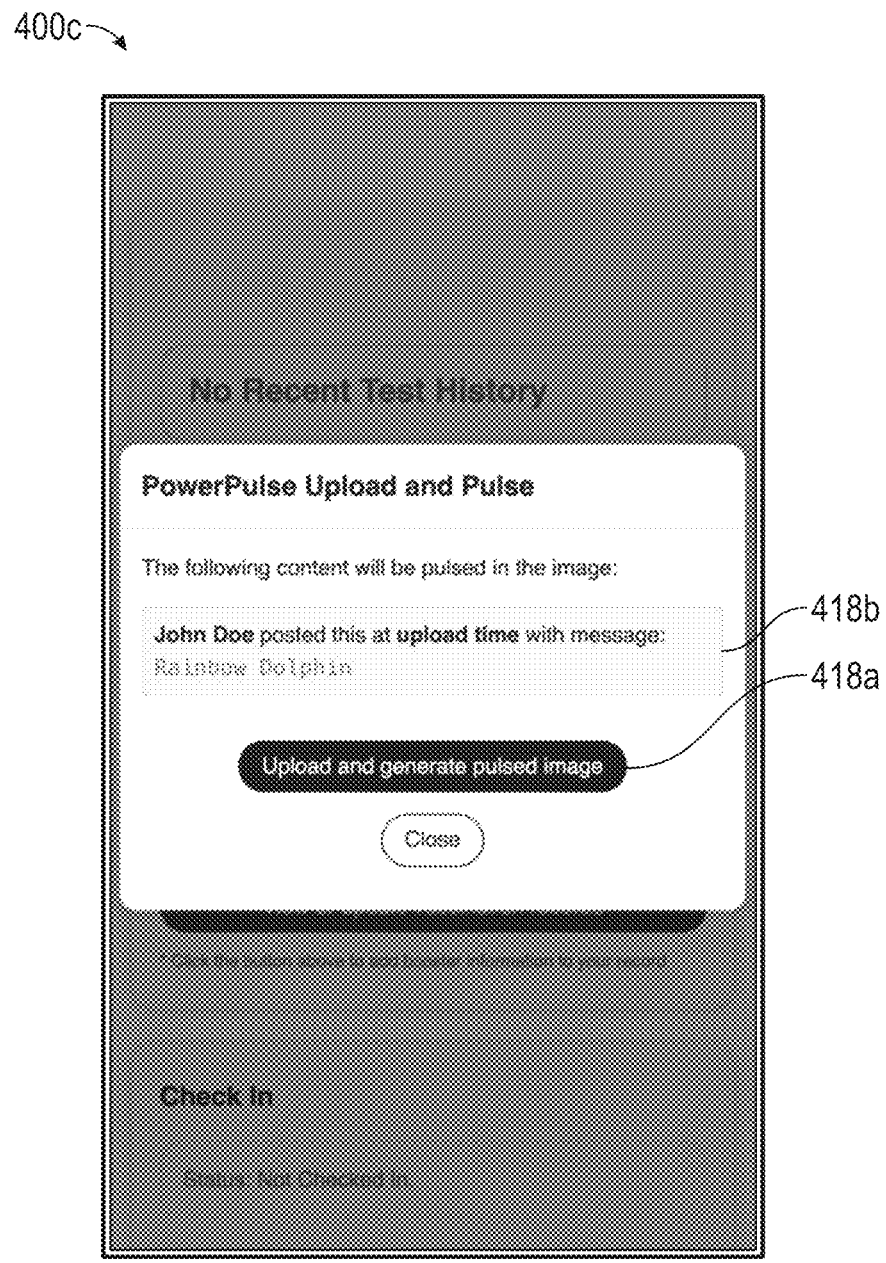
FIG. 4C is another example screen depicting another embodiment of encoding the content by the content encoding and decoding module, in accordance with one or more exemplary embodiments.

Referring to FIG. 4C is another example screen 400*c* depicting another embodiment of encoding the content by the content encoding and decoding module, in accordance with one or more exemplary embodiments. The screen 400*c* depicts upload and generate pulsed image option 418*a*, posted content displaying bar 418*b*. The upload and generate pulsed image option 418*a* may be configured to enable the first user and the second user to upload the image and embed the pulse code for generating the pulsed image. The posted content displaying bar 418*b* may be configured to display the content selected to upload along with the message.

Figure 4D:
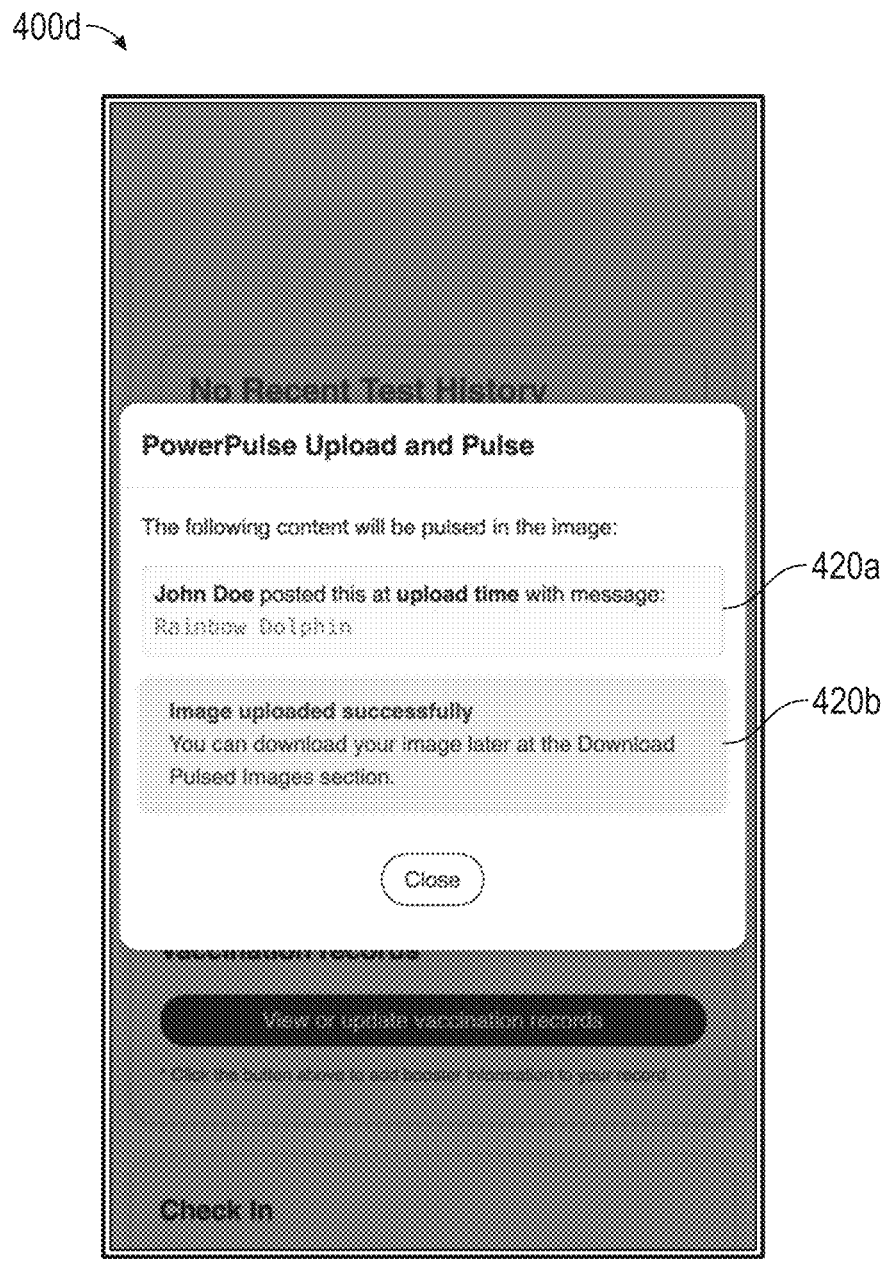
FIG. 4D is another example screen depicting another embodiment encoding the content by the content encoding and decoding module, in accordance with one or more exemplary embodiments.

Referring to FIG. 4D is another example screen 400*d* depicting another embodiment encoding the content by the content encoding and decoding module, in accordance with one or more exemplary embodiments. The screen 400*d* depicts posted content and messages displaying bar 420*a* and a status displaying bar 420*b*. The posted content and message displaying bar 420*a* may be configured to display the uploaded content to be pulsed along with the message. The status displaying bar 420*b* may be configured to display the status of the content uploaded on the first computing device 102 and the second computing device 104. The status of the content may include, but is not limited to, uploaded successfully, uploading failed, uploading pending, and the like.

Figure 4E:
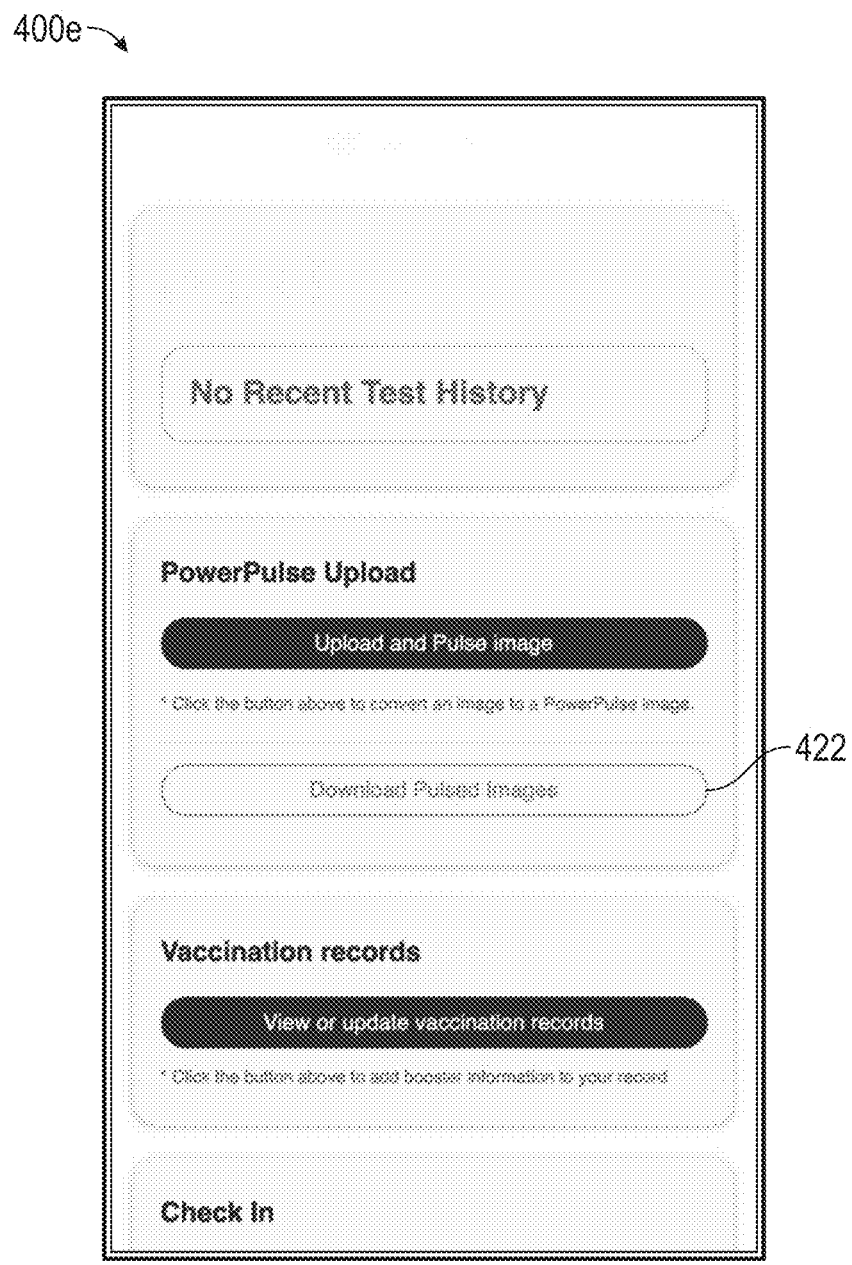
FIG. 4E, and FIG. 4F are example screens depicting embodiments of encoding the content by the content encoding and decoding module, in accordance with one or more exemplary embodiments.
Figure 4F:
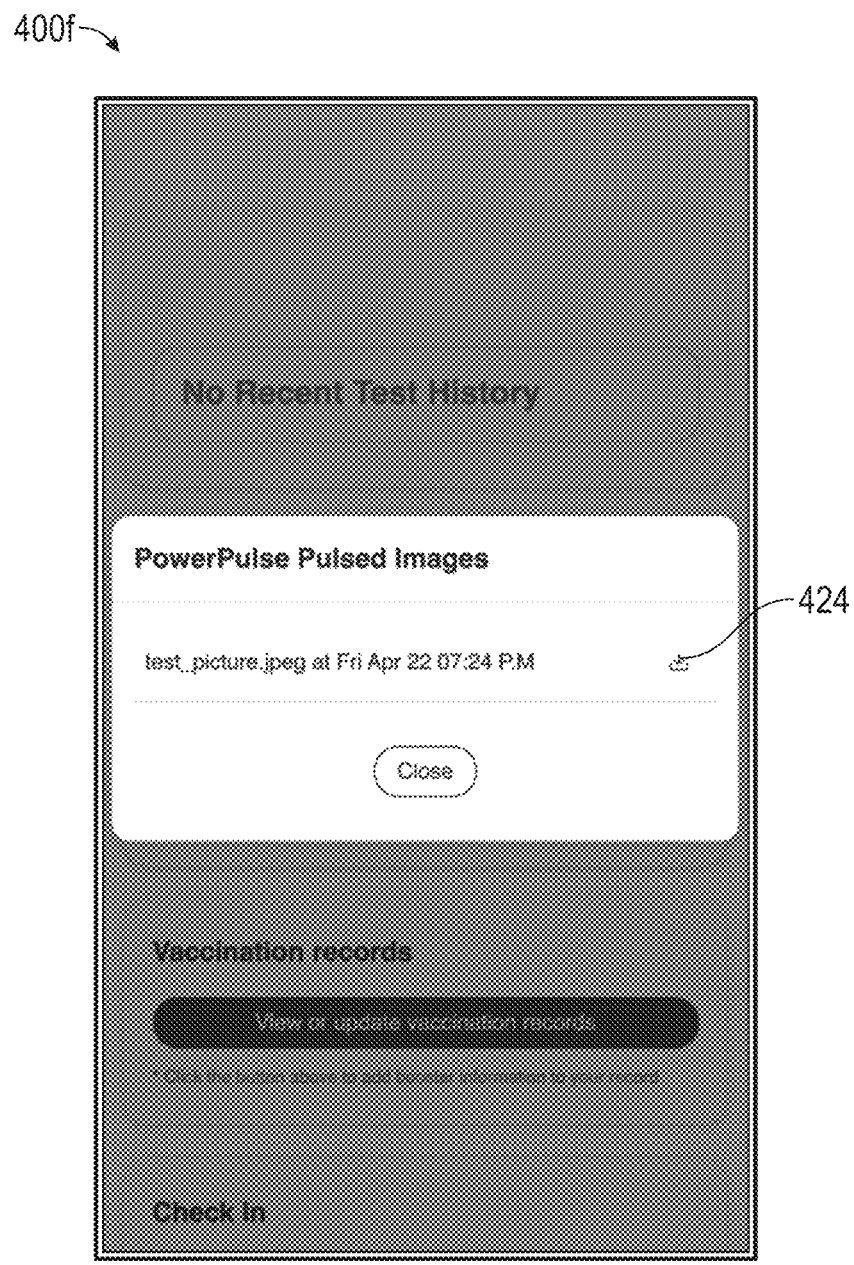

Referring to FIG. 4E, and FIG. 4F are example screens 400*e*, 400*f* depicting embodiments of encoding the content by the content encoding and decoding module, in accordance with one or more exemplary embodiments. The example screen 400*e* depicts download pulsed image option 422 configured to display the pulsed image/picture on the first computing device 102 and the second computing device 104. The screen 400*f* depicts a download icon 424 configured to enable the first user or the second user to download the pulsed image on the first computing device 102 and the second computing device 104.

In accordance with one or more exemplary embodiments of the present disclosure, the pulse oracle 124 functionality to create a pulse template, and then enabling the first user to choose which fields (MicroPulses) are to be part of that template. The first user may be able to edit existing pulse templates or create new pulse templates. Once the first user selects an existing, or creates a new template, the content encoding and decoding module 116 may be configured to enable the first user to select from a list of existing Micro-Pulses to include in the template.

Figure 5A:
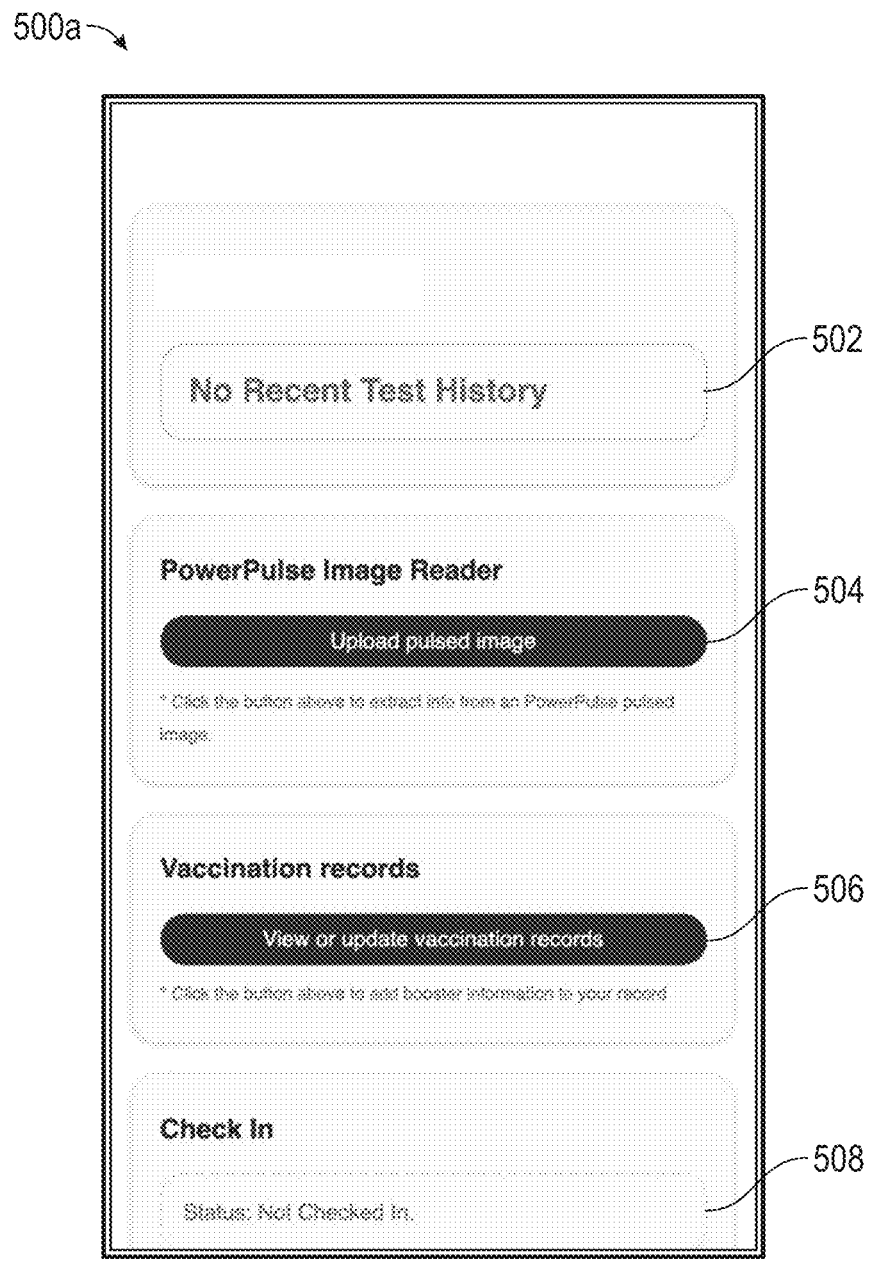
FIG. 5A is an example screen depicting an embodiment of decoding the content by the content encoding and decoding module, in accordance with one or more exemplary embodiments.

Referring to FIG. 5A is an example screen 500*a* depicting an embodiment of decoding the content by the content encoding and decoding module, in accordance with one or more exemplary embodiments. The screen 500*a* depicts a no recent test history option 502, upload pulsed image option 504, view or update vaccination records option 506, and a check-in option 508. The no recent test history option 502 may be configured to enable the first user or the second user to review the recent history of the content selected from the first computing device 102 or the second computing device 104. The upload pulsed image option 504 may be configured to enable the first user or the second user to extract the pulse information from the pulsed content on the first computing device 102 or the second computing device 104. The view or update vaccination records option 506 may be configured to enable the first user or the second user to review the pulsed vaccination records and to add the booster dose information to the first or second user records. The check-in option 508 may be configured to enable the first user and the second user to check the status of the uploaded content.

Figure 5B:
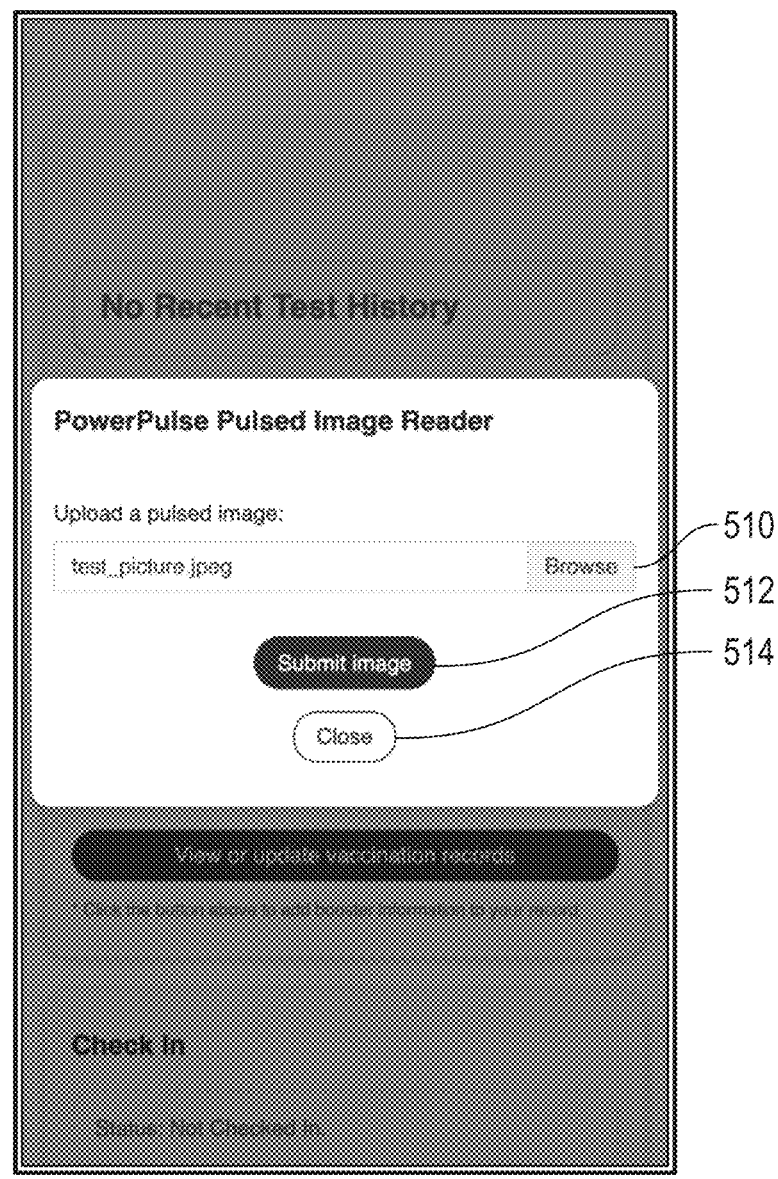
FIG. 5B is another example screen depicting another embodiment of decoding the content encoding and decoding module, in accordance with one or more exemplary embodiments.

Referring to FIG. 5B is another example screen 500*b* depicting another embodiment of decoding the content encoding and decoding module, in accordance with one or more exemplary embodiments. The screen 500*b* depicts the browse option 510, a submit image option 512, and a close option 514. The browse option 510 may be configured to enable the first User or the second User to browse and upload the pulsed content received from the first computing device 102 or the second computing device 104. The submit image option 512 may be configured to enable the first User or the second User to view the content on the first computing device 102 and the second computing device 104 by decoding the pulse codes embedded in the content.

Figure 5C:
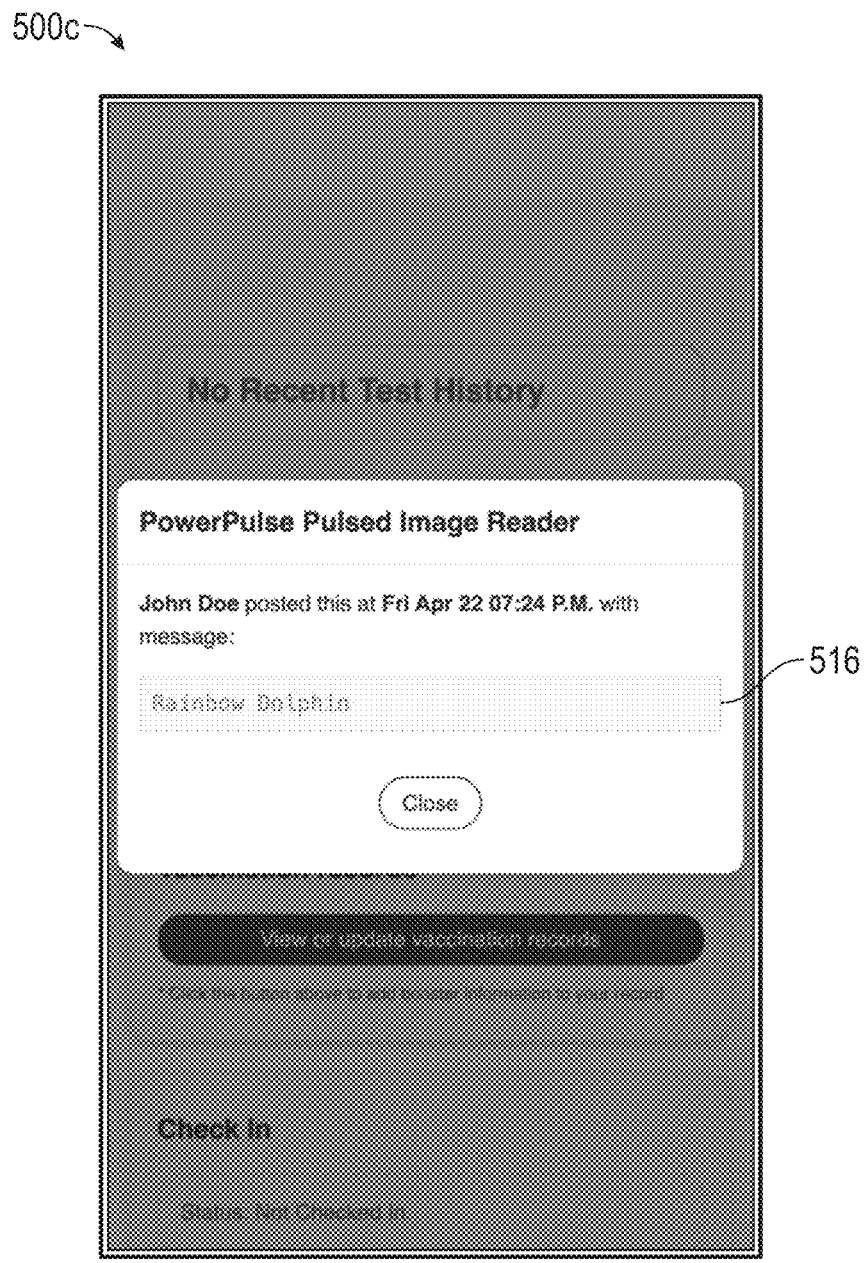
FIG. 5C is another example screen depicting another embodiment of decoding the content by the content encoding and decoding module, in accordance with one or more exemplary embodiments.

Referring to FIG. 5C is another example screen 500*c* depicting another embodiment of decoding the content by the content encoding and decoding module, in accordance with one or more exemplary embodiments. The screen 400*c* includes a message bar 516. The message bar 516 may be configured to display a message along with the decoded content displayed on the first computing device 102 and the second computing device 104.

In accordance with one or more exemplary embodiments of the present disclosure, the external data sources (for example, external database) may be configured to pull MicroPulse values and populate the pulse by the pulse injector 120. Many different types of data sources and connections may be configured from Public APIs, to SQL, NOSQQL, or any other type of secure authenticated data sources. User profiles, and security clearance may be populated here by connecting to a corporate user database and utilizing real-time secure transfers enabling the levels of pulse-protected data users can access. Each data source may return a file, single value or an entire data structure such as an array, a list, or a set of key-value pairs. Once each data-source is configured, the pulse injector may be programmatically and automatically pull and inject the data on user basis as the values per user may be varied.

Figure 6:
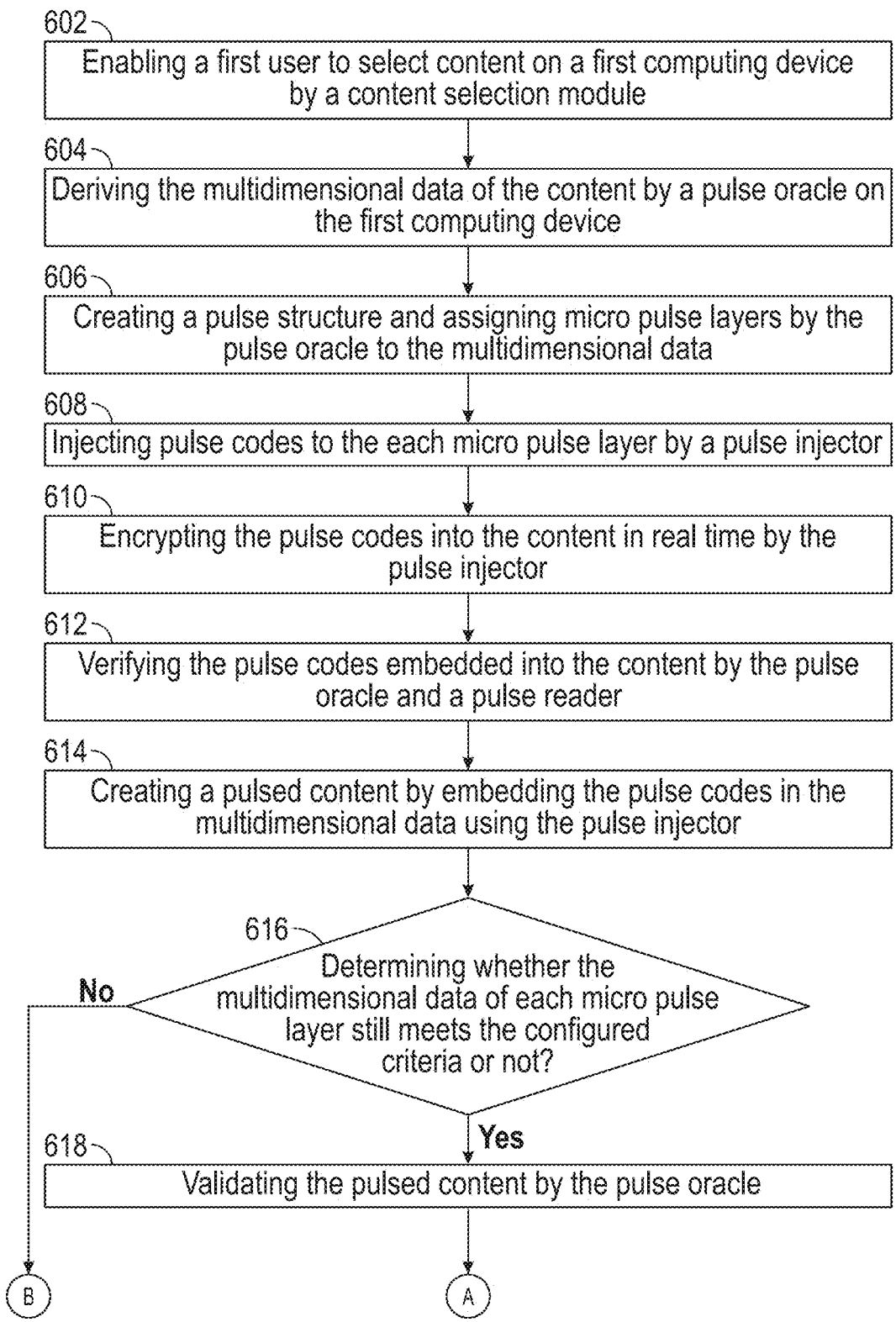
FIG. 6 is a flow diagram depicting a method for detecting an unauthorized user attempting to authenticate the content in real-time, in accordance with one or more exemplary embodiments.
Figure 6:
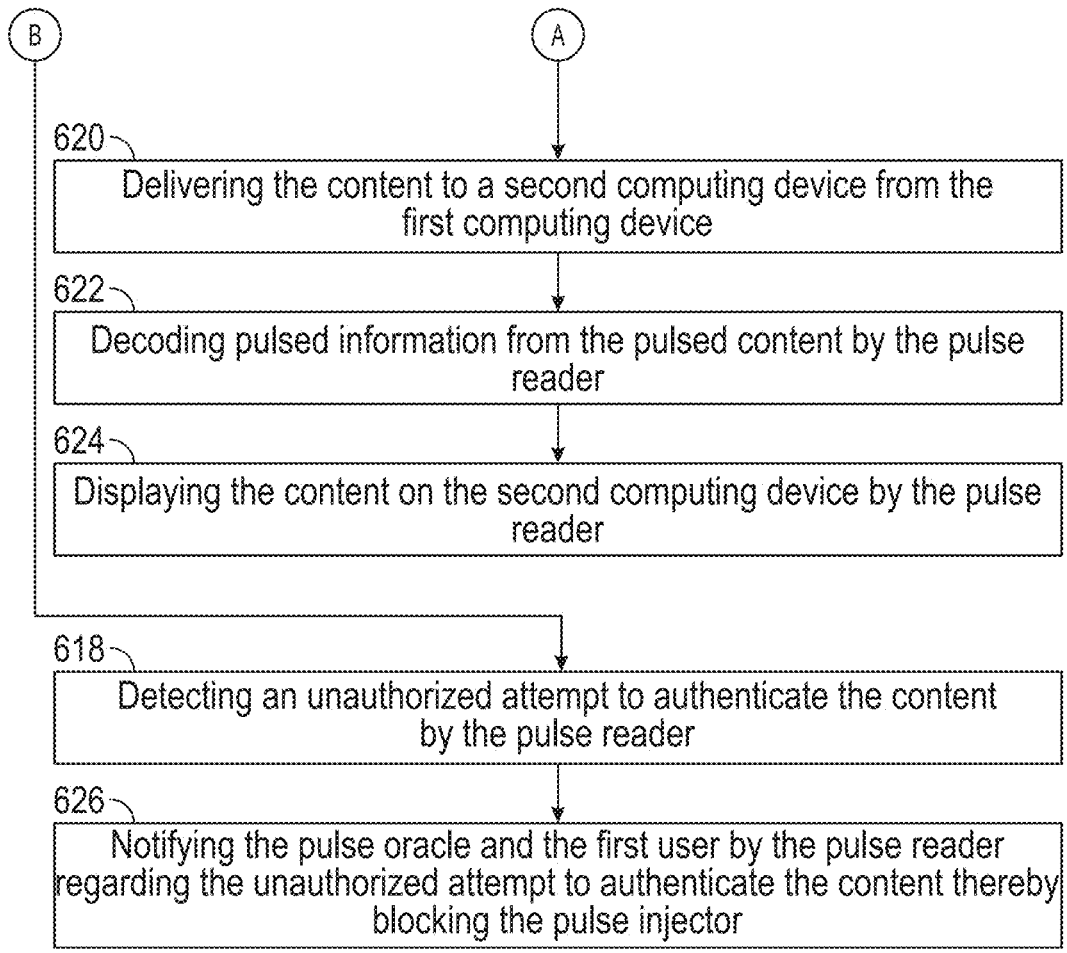

Referring to FIG. 6 is a flow diagram 600 depicting a method for detecting an unauthorized user attempting to authenticate the content in real-time, in accordance with one or more exemplary embodiments. The method 600 may be carried out in the context of the details of FIG. 1A, FIG. 1B, FIG. 2, FIG. 3, FIG. 4A, FIG. 4B, FIG. 4C, FIG. 4D, FIG. 4E, FIG. 4F, FIG. 5A, FIG. 5B, and FIG. 5C. However, the method 600 may also be carried out in any desired environment. Further, the aforementioned definitions may equally apply to the description below.

The method commences at step 602, enabling the first user to select the content on the first computing device by the content selection module. Thereafter at step 604, deriving the multidimensional data of the content by the pulse oracle on the first computing device. Thereafter at step 606, creating the pulse structure and assigning the micropulse layers by the pulse oracle to the multidimensional data. Thereafter at step 608, injecting pulse codes to each micropulse layer by the pulse injector. Thereafter at step 610, encrypting the pulse codes into the content in real time by the pulse injector. Thereafter at step 612, verifying the pulse codes embedded into the content by the pulse oracle and the pulse reader. Thereafter at step 614, creating the pulsed content by embedding the pulse codes in the multidimensional data using the pulse injector. At step 616, determining whether the multidimensional data of each micropulse layer still meets the configured criteria or not? If the answer at step 618 is Yes, validating the pulsed content by the pulse oracle. Thereafter at step 620, delivering the content to the second computing device from the first computing device. Thereafter at step 622, decoding pulse information from the pulsed content by the pulse reader. Thereafter at step 624, displaying the content on the second computing device by the pulse reader. If the answer at step 618 is No, detecting an unauthorized attempt to authenticate the content by the pulse reader. Thereafter at step 626, notifying the pulse oracle and the first user by the pulse reader regarding the unauthorized attempt to authenticate the content thereby blocking the pulse injector.

Figure 7:
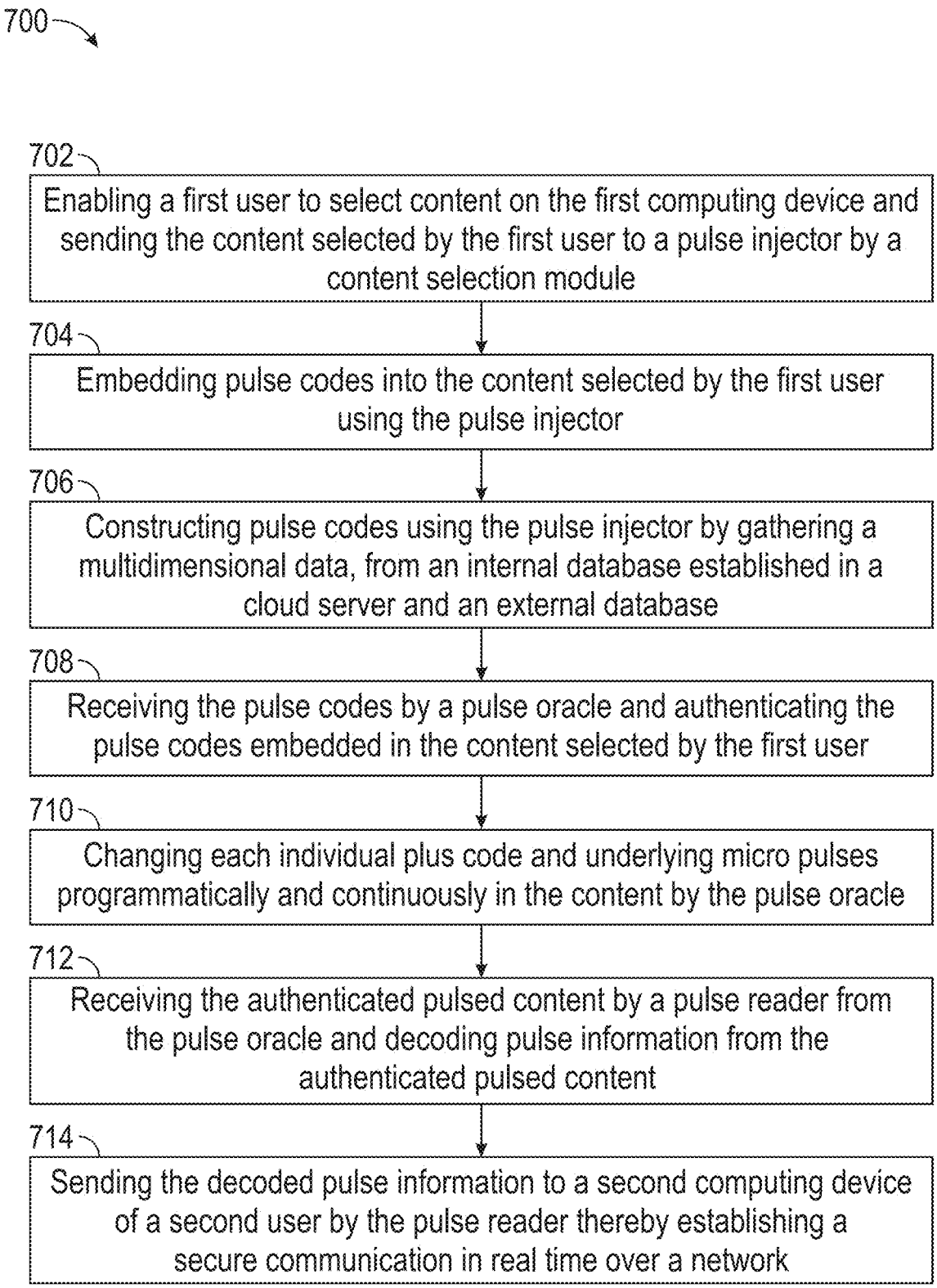
FIG. 7 is a flow diagram depicting a method for establishing secure communication in real-time, in accordance with one or more exemplary embodiments.

Referring to FIG. 7 is a flow diagram 700 depicting a method for establishing secure communication in real-time, in accordance with one or more exemplary embodiments. The method 700 may be carried out in the context of the details of FIG. 1A, FIG. 1B, FIG. 2, FIG. 3, FIG. 4A, FIG. 4B, FIG. 4C, FIG. 4D, FIG. 4E, FIG. 4F, FIG. 5A, FIG. 5B, FIG. 5C and FIG. 6. However, the method 700 may also be carried out in any desired environment. Further, the aforementioned definitions may equally apply to the description below.

The method commenced at step 702, enabling the first user to select the content (static content/dynamic content) on the first computing device and sending the content selected by the first user to the pulse injector by the content selection module. Thereafter at step 704, embedding the pulse codes into the content selected by the first user using the pulse injector. Thereafter at step 706, constructing the pulse codes using the pulse injector by gathering the multidimensional data, from the internal database established in the cloud server and the external database. Thereafter at step 708, receiving the pulse codes by the pulse oracle and authenticating the pulse codes embedded in the content selected by the first user. Thereafter at step 710, changing each individual pulse code and underlying micro pulses programmatically and continuously in the content by the pulse oracle. Thereafter at step 712, receiving the authenticated pulsed content by a pulse reader from the pulse oracle and decoding the pulse information from the authenticated pulsed content by the pulse reader. Thereafter at step 714, sending the decoded pulse information to the second computing device of the second user by the pulse reader thereby establishing the secure communication in real time over the network.

Referring to FIG. 8 is a block diagram 800 illustrating the details of a digital processing system 800 in which various aspects of the present disclosure are operative by execution of appropriate software instructions. The Digital processing system 800 may correspond to the first computing device 102 or second computing device 104 (or any other system in which the various features disclosed above can be implemented).

Digital processing system 800 may contain one or more processors such as a central processing unit (CPU) 810, random access memory (RAM) 820, secondary memory 830, graphics controller 860, display unit 870, network interface 880, and input interface 890. All the components except display unit 870 may communicate with each other over communication path 850, which may contain several buses as is well known in the relevant arts. The components of FIG. 8 are described below in further detail.

CPU 810 may execute instructions stored in RAM 820 to provide several features of the present disclosure. CPU 810 may contain multiple processing units, with each processing unit potentially being designed for a specific task. Alternatively, CPU 810 may contain only a single general-purpose processing unit. CPU 810 may be a physical processor or a virtual processor with a virtual machine or containerized system.

RAM 820 may receive instructions from secondary memory 830 using communication path 850. RAM 820 is shown currently containing software instructions, such as those used in threads and stacks, constituting shared environment 825 and/or user programs 826. Shared environment 825 includes operating systems, device drivers, virtual machines, etc., which provide a (common) run time environment for execution of user programs 826. RAM 820 may be a physical component or a virtual component within a virtual machine or containerized system such as a Docker.

Graphics controller 860 generates display signals (e.g., in RGB format) to display unit 870 based on data/instructions received from CPU 810. Display unit 870 contains a display screen to display the images defined by the display signals. Input interface 890 may correspond to a keyboard and a pointing device (e.g., touch-pad, mouse) and may be used to provide inputs. Network interface 880 provides connectivity to a network (e.g., using Internet Protocol), and may be used to communicate with other systems (such as those shown in FIG. 1) connected to the network 106. Graphics controller 860 may be a physical component or a virtual component within a virtual machine or containerized system such as Docker.

Secondary memory 830 may contain hard drive 835, flash memory 836, and removable storage drive 837. Secondary memory 830 may store the data software instructions (e.g., for performing the actions noted above with respect to the Figures), which enables digital processing system 800 to provide several features in accordance with the present disclosure. Secondary memory 830 may be a physical component or a virtual component within a virtual machine or containerized system such as Docker.

Some or all of the data and instructions may be provided on removable storage unit 840, and the data and instructions may be read and provided by removable storage drive 837 to CPU 810. Floppy drive, magnetic tape drive, CD-ROM drive, DVD Drive, Flash memory, removable memory chip (PCMCIA Card, EEPROM) are examples of such removable storage drive 837.

Removable storage unit 840 may be implemented using medium and storage format compatible with removable storage drive 837 such that removable storage drive 837 can read the data and instructions. Thus, removable storage unit 840 includes a computer readable (storage) medium having stored therein computer software and/or data. However, the computer (or machine, in general) readable medium can be in other forms (e.g., non-removable, random access, etc.).

In this document, the term "computer program product" is used to generally refer to removable storage unit 840 or hard disk installed in hard drive 835. These computer program products are means for providing software to digital processing system 800. CPU 810 may retrieve the software instructions, and execute the instructions to provide various features of the present disclosure described above.

The term "storage media/medium" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage memory 830. Volatile media includes dynamic memory, such as RAM 820. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus (communication path) 850. Transmission media can also take the form of acoustic or light waves, such as those generated during radio-wave and infra-red data communications.

Reference throughout this specification to "one embodiment", "an embodiment", or similar language means that a particular feature, structure, or characteristic described in connection with the embodiment is included in at least one embodiment of the present disclosure. Thus, appearances of the phrases "in one embodiment", "in an embodiment" and similar language throughout this specification may, but do not necessarily, all refer to the same embodiment.

Furthermore, the described features, structures, or characteristics of the disclosure may be combined in any suitable manner in one or more embodiments. In the above description, numerous specific details are provided such as examples of programming, software modules, user selections, network transactions, database queries, database structures, hardware modules, hardware circuits, hardware chips, etc., to provide a thorough understanding of embodiments of the disclosure.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub-combinations of the various features described hereinabove as well as variations and modifications thereof, which would occur to persons skilled in the art upon reading the foregoing description.

In another embodiment of the present disclosure, a system for establishing a secure communication in real-time, the system includes the first computing device 102, the second computing device 104, and the cloud server 108. The content encoding and decoding module 116, and the content encoding and decoding module 116 further includes the content selection module 118, the pulse injector 120, and the pulse reader 122.

In another embodiment of the present disclosure, the cloud server 108 includes the pulse oracle 124, the pulse data manager 126, and the internal database 128. The content selection module 118 enables the first user to select content on the first computing device 102 and send the digital content selected by the first user to the pulse injector 120. The pulse injector 120 embeds pulse codes into the content selected by the first user, the pulse injector 120 construct pulse codes by gathering a multidimensional data, from at least one internal database 128 established in the cloud server 108 and the external database 110.

In another embodiment of the present disclosure, the pulse oracle 124 and the pulse reader 122 are synchronized to receive the pulse codes and authenticates the pulse codes embedded in the content selected by the first user, the pulse oracle 124 changes each individual pulse code and underlying micro pulses programmatically and continuously in the content.

In another embodiment of the present disclosure, the pulse reader 122 receives the authenticated pulsed content selected by the first user from the pulse oracle 124 and decodes pulse information from the authenticated pulsed content, the pulse reader 122 sends the decoded pulse information to the second computing device 104 of the second user and establishes the secure communication in real time over the network 106.

In another embodiment of the present disclosure, the pulse injector 120 is configured to create a user-specific pulse object and encrypt, embed, and hide the pulse codes into the content in real time. The pulse injector 120 is configured to reside the pulse codes injected into the content encrypted and hidden using various techniques depending on the content type. The pulse injector 120 is dynamically configurable, and capable of maintaining a synchronous, asynchronous, uni or bidirectional communication with the pulse oracle 124 depending on the needs of an application.

In another embodiment of the present disclosure, the pulse oracle 124 is configured to create pulse templates and declares acceptable thresholds of the digital content for each MicroPulse (Pulse Target). The pulse oracle 124 is configured to distribute the pulse templates and pulse targets to the other components of the system. The pulse oracle 124 is configured to monitor a payload of rejected payloads. The pulse oracle 124 is configured to change the pulse templates and/or the pulse targets dynamically and in real-time to strengthen security and make brute force attacks more difficult when an intrusion is suspected or an anomaly detected. The pulse oracle 124 is configured to create a pulse structure by configuring the content specific layers. The pulse oracle 124 is configured to analyze incorrect or unauthorized pulses, and the offending MicroPulses for forensic analysis. The pulse oracle 124 is configured to react continuously by changing the pulse structure and the target values of the micro pulse codes when an intruder attempts to brute force the secure connection.

In another embodiment of the present disclosure, the pulse reader 122 is programmatically start logics and actions, or certify authenticity. The pulse reader 122 is configured to read, unhide, and unencrypt the pulse information/objects embedded in the pulse codes. The pulse reader 122 is configured to synchronize with the pulse reader 122 and sets instructions on how to handle MicroPulse decode, and what application, technical, or operational steps to perform depending on the pulsed content received from at least one of the computing devices 102/104. The pulse reader 122 notifies the pulse oracle 124 of the status of pulse decoding.

In another embodiment of the present disclosure, the pulse data manager 126 functions as an intermediary and staging area for all data types delivering data to the pulse oracle 124 and other components of the system in real-time. The pulse data manager 126 is configured to apply application logic and transformations to engineer the data-features that are needed to embed into the pulse codes as well as perform any logical comparisons, calculations, and transformations that are needed for reporting, application-export, and other actions. The pulse data manager 126 functions as a firewall for data leakage and data isolation.

What is claimed is:

1. A system for establishing a secure communication in real-time, the system comprises:
   A first computing device;
   A second computing device;
   A cloud server;
   wherein at least one computing device comprises a content encoding and decoding module, the content encoding and decoding module comprising a content selection module, a pulse injector, and a pulse reader;
   the cloud server comprising a pulse oracle, a pulse data manager and an internal database; wherein
   the content selection module comprises software instructions executed by a processor, enabling a first user to select content on the first computing device through an user interface and send the content selected by the first user to the pulse injector for processing, whereby the pulse injector being configured to construct and embeds one or more pulse codes into the content using multi-dimensional data retrieved from at least one of: an internal database established in the cloud server; and at least one external database;
   the pulse oracle synchronizes with the pulse injector by distributing pulse templates and configuring security settings, such as session keys, to secure the embedded pulse codes, whereby the pulse oracle programmatically manages the security settings and continuously updates them based on predefined security elements, authenticates the pulse codes to verify their integrity, and dynamically adjusts the pulse codes to counter unauthorized access attempts;
   the pulse reader receives the authenticated pulsed content selected by the first user from the pulse oracle and decodes pulse information from the authenticated pulsed content, whereby the pulse reader sends the decoded pulse information to the second computing device of a second user and establishes a secure communication in real time over the network.

2. The system of claim 1, wherein the pulse injector includes elements that generate a user-specific pulse object to encrypt and embed the one or more pulse codes within the content in real time.

3. The system of claim 1, wherein the pulse injector includes components that encrypt and hide the one or more pulse codes within the content using techniques selected based on the content type.

4. The system of claim 1, wherein the pulse injector is configurable to maintain a synchronous or asynchronous, uni or bidirectional communication with the pulse oracle, based on the requirements of the application.

5. The system of claim 1, wherein the pulse oracle generates one or more pulse templates and specifies acceptable thresholds for the content associated with each MicroPulse (Pulse Target).

6. The system of claim 1, wherein the pulse oracle distributes the one or more pulse templates and pulse targets to other components of the system.

7. The system of claim 1, wherein the pulse oracle monitors a payload of one or more rejected payloads.

8. The system of claim 1, wherein the pulse oracle changes the one or more pulse templates and/or pulse targets dynamically in real-time to strengthen security and make brute force attacks more difficult when an intrusion is suspected or an anomaly detected.

9. The system of claim 1, wherein the pulse oracle creates a pulse structure by configuring content specific layers.

10. The system of claim 1, wherein the pulse oracle analyzes incorrect or unauthorized pulses and identifies the offending MicroPulses for forensic analysis.

11. The system of claim 1, wherein the pulse oracle reacts by continuously changing the pulse structure and the target values of the micro pulse codes when an intruder attempts to brute force the secure connection.

12. The system of claim 1, wherein the pulse reader performs logic-based actions or certifies authenticity programmatically.

13. The system of claim 1, wherein the pulse reader reads, unhides, and unencrypts the pulse information or objects embedded in the one or more pulse codes.

14. The system of claim 1, wherein the pulse reader synchronizes with the pulse oracle and sets instructions on handling MicroPulse decoding and determining which application, technical, or operational steps to perform on the pulsed content received from the computing device.

15. The system of claim 1, wherein the pulse reader communicates the status of pulse decoding to the pulse oracle.

16. The system of claim 1, wherein the pulse data manager functions as an intermediary and staging area for all data types, delivering data to the pulse oracle and other system components in real-time.

17. The system of claim 1, wherein the pulse data manager applies application logic and transform data features needed for embedding into the one or more pulse codes, and performs logical comparisons, calculations, and transformations required for reporting, application-export, and other actions.

18. The system of claim 1, wherein the pulse data manager functions as a firewall to prevent data leakage and ensure data isolation.

19. A method for establishing a secure communication in real-time, the method comprises:
- A first computing device;
- A second computing device;
- A cloud server;
- whereby at least one computing device comprises a content encoding and decoding module, and the content encoding and decoding module further comprises a content selection module, a pulse injector, and a pulse reader;
- the cloud server comprises a pulse oracle, a pulse data manager and an internal database;
- enabling a first user to select content on the first computing device and sending the content selected by the first user to the pulse injector by the content selection module;
- embedding one or more pulse codes into the content using the pulse injector, the content is selected by the first user;
- constructing one or more pulse codes using the pulse injector by gathering a multidimensional data, from at least one internal database established in the cloud server and an external database;
- receiving the one or more pulse codes by the pulse oracle and authenticating the one or more pulse codes embedded in the content selected by the first user;
- changing each individual pulse code and underlying micro pulses programmatically and continuously in the content by the pulse oracle;
- receiving the authenticated pulsed content by the pulse reader from the pulse oracle and decoding pulse information from the authenticated pulsed content; and
- sending the decoded pulse information to the second computing device of a second user by the pulse reader thereby establishing a secure communication in real time over the network.

20. A computer program product comprising a non-transitory computer-readable medium having a computer-readable program code embodied therein to be executed by one or more processors, the program code including instructions to:
- enable a first user to select content on the first computing device and sending the content selected by the first user to the pulse injector by the content selection module;
- embed one or more pulse codes into the content using the pulse injector, the content is selected by the first user;
- construct one or more pulse codes using the pulse injector by gathering a multidimensional data, from at least one internal database established in the cloud server and an external database;
- receive the one or more pulse codes by the pulse oracle and authenticating the one or more pulse codes embedded in the content selected by the first user;
- change each individual pulse code and underlying micro pulses programmatically and continuously in the content by the pulse oracle;
- receive the authenticated pulsed content by the pulse reader from the pulse oracle and decoding pulse information from the authenticated pulsed content; and
- send the decoded pulse information to the second computing device of a second user by the pulse reader thereby establishing a secure communication in real time over the network.

* * * * *